United States Patent
Masatomi et al.

(10) Patent No.: US 9,415,001 B2
(45) Date of Patent: Aug. 16, 2016

(54) LIQUID ARYL GROUP-CONTAINING POLYORGANOSILOXANE

(71) Applicant: Dow Corning Toray Co., Ltd., Tokyo (JP)

(72) Inventors: Toru Masatomi, Ichihara (JP); Jun Miyano, Ichihara (JP); Satoshi Onodera, Ichihara (JP); Yasue Kanzaki, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/407,729

(22) PCT Filed: Mar. 8, 2013

(86) PCT No.: PCT/JP2013/057328
§ 371 (c)(1),
(2) Date: Dec. 12, 2014

(87) PCT Pub. No.: WO2013/161429
PCT Pub. Date: Oct. 31, 2013

(65) Prior Publication Data
US 2015/0164774 A1 Jun. 18, 2015

(30) Foreign Application Priority Data

Apr. 23, 2012 (JP) .................................. 2012-098200
Oct. 22, 2012 (JP) .................................. 2012-232543

(51) Int. Cl.
*A61K 8/891* (2006.01)
*C08G 77/04* (2006.01)
(Continued)

(52) U.S. Cl.
CPC . *A61K 8/891* (2013.01); *A61K 8/92* (2013.01); *A61Q 1/04* (2013.01); *A61Q 1/06* (2013.01);
(Continued)

(58) Field of Classification Search
None
See application file for complete search history.

(56) References Cited

U.S. PATENT DOCUMENTS 3,389,159 A * 6/1968 Nielsen ................. C07F 7/0849
556/452
4,289,891 A * 9/1981 Brown, Jr. ............. C07F 7/0849
252/78.3
(Continued)

FOREIGN PATENT DOCUMENTS

CN 101787133 A 7/2010
JP S62234012 A 10/1987
(Continued)

OTHER PUBLICATIONS

English language abstract for JPS62234012 extracted from espacenet.com database on Jan. 29, 2015, 2 pages.
(Continued)

*Primary Examiner* — Robert S Loewe
(74) *Attorney, Agent, or Firm* — Howard & Howard Attorneys PLLC

(57) ABSTRACT

A liquid aryl group-containing polyorganosiloxane comprising an arylsiloxy unit represented by $RSiO_{3/2}$ (wherein R is an aryl group), wherein: the arylsiloxy unit constitutes from 20 to 50 mol % of all the siloxy units constituting the polymer, and an average number of moles of aryl groups per 1 mole of Si atoms in the molecule is within a range of 1.20 to 1.65. A composition with an oil agent of the same, wherein the overall refractive index of the composition is not less than 1.45, and an overall viscosity at 25° C. of the composition is in a range from 100 to 100,000 mPa·s.

14 Claims, 3 Drawing Sheets

(51) Int. Cl.

| | | |
|---|---|---|
| C08L 83/04 | (2006.01) | |
| C08G 77/00 | (2006.01) | |
| A61Q 1/04 | (2006.01) | |
| A61Q 1/06 | (2006.01) | |
| A61Q 1/10 | (2006.01) | |
| A61Q 5/06 | (2006.01) | |
| A61Q 17/04 | (2006.01) | |
| A61K 8/92 | (2006.01) | |
| A61Q 1/08 | (2006.01) | |
| A61Q 1/12 | (2006.01) | |
| A61Q 19/00 | (2006.01) | |

(52) U.S. Cl.
CPC .. *A61Q 1/10* (2013.01); *A61Q 5/06* (2013.01); *A61Q 17/04* (2013.01); *A61Q 19/001* (2013.01); *C08G 77/04* (2013.01); *C08G 77/045* (2013.01); *C08G 77/70* (2013.01); *C08G 77/80* (2013.01); *C08L 83/04* (2013.01); *A61Q 1/08* (2013.01); *A61Q 1/12* (2013.01); *A61Q 19/00* (2013.01)

(56) References Cited

U.S. PATENT DOCUMENTS

| | | |
|---|---|---|
| 2008/0305062 A1 | 12/2008 | Bui et al. |
| 2011/0110873 A1* | 5/2011 | Horstman ............ A61K 8/0229 424/59 |
| 2013/0023591 A1 | 1/2013 | Shoji et al. |

FOREIGN PATENT DOCUMENTS

| | | |
|---|---|---|
| JP | H01168607 A | 7/1989 |
| JP | H07089844 A | 4/1995 |
| JP | 2007535586 A | 12/2007 |
| JP | 2009019033 A | 1/2009 |
| JP | 2011136935 A | 7/2011 |
| WO | WO2005/090444 A1 | 9/2005 |
| WO | WO 2010/103103 A1 | 9/2010 |
| WO | WO2011081218 A1 | 7/2011 |

OTHER PUBLICATIONS

English language abstract for JPH01168607 extracted from espacenet.com database on Jan. 29, 2015, 2 pages.
English language abstract and machine-assisted English translation for JPH07089844 extracted from PAJ database on Jan. 29, 2015, 25 pages.
English language abstract not found for JP2007535586; however, see English language equivalent WO 2005-090444. Original document extracted from espacenet.com database on Jan. 19, 2015, 19 pages.
English abstract for JP20090109033 extracted from espacenet.com database on Jan. 19, 2015, 1 page.
English abstract for JP2011136935 extracted from espacenet.com database on Jan. 19, 2015, 2 pages.
International Search Report for PCT/JP2013/057328 dated Jul. 4, 2013, 3 pages.
Partial English language translation of The Nikkan Kogyo Shimbun, Ltd. "Silicone Handbook," Aug. 31, 1990, p. 404, provided by Dow Corning Toray, Ltd. on Mar. 14, 2015.
Partial English language translation of Dow Corning Toray, Ltd., "Personal Care Silicone No. Y517 Catalog", Feb. 1, 2009, p. 13, provided by Dow Corning Toray, Ltd. on Mar. 14, 2015.
English language abstract and machine-assisted English translation for CN 101787133 extracted from espacenet.com database on Apr. 4, 2016, 15 pages.
English language abstract and machine-assisted English translation for WO 2010/103103 extracted from espacenet.com database on Apr. 4, 2016, 38 pages.

* cited by examiner

LIQUID ARYL GROUP-CONTAINING POLYORGANOSILOXANE

RELATED APPLICATIONS

This application is the National Stage of International Patent Application No. PCT/JP2013/057328, filed on Mar. 8, 2013, which claims priority to and all the advantages of Japanese Patent Application No. 2012-098200, filed on Apr. 23, 2012, and Japanese Patent Application No. 2012-232543, filed on Oct. 22, 2012, the contents of which are incorporated herein by reference.

TECHNICAL FIELD

The present invention relates to a novel liquid aryl group-containing organopolysiloxane having a branched structure that is liquid and has a high content of aryl groups (primarily phenyl groups or naphthyl groups). As a result of such a configuration, a high refractive index is displayed and compatibility with oil agents or oleophilic components is superior. Furthermore, in cases where mixed with an oil agent, the novel liquid aryl group-containing organopolysiloxane can be stably compounded in a non-aqueous cosmetic composition without turbidity that accompanies hydrolysis occurring when stored for an extended period of time, an appearance with depth is imparted using a small amount, makeup running does not easily occur, and the durability of cosmetic effects is superior. Additionally, hair cosmetic composition combined with the novel liquid aryl group-containing organopolysiloxane imparts excellent frizz control benefit to human hair. Moreover, the present invention relates to an aryl group-containing polyorganosiloxane composition and a cosmetic composition comprising the novel liquid aryl group-containing organopolysiloxane; and a simple method of producing the liquid organopolysiloxane. The novel liquid aryl group-containing organopolysiloxane according to the present invention can be used in the same applications recited for the cosmetic raw material and the glossy cosmetic composition described in Japanese Unexamined Patent Application Publication No. 2011-136935 proposed by the present applicant. Likewise, a composition comprising the novel liquid aryl group-containing organopolysiloxane according to the present invention and an oil agent can be used in the same applications recited for the phenyl silsesquioxane resin compositions described in Japanese Unexamined Patent Application Publication (Translation of PCT Application) No. 2007-535586 and Japanese Unexamined Patent Application Publication No. 2009-019033.

BACKGROUND ART

Silicone resins having phenyl groups and methylphenylpolysiloxanes that are exemplary of phenylsilsesquioxane resins are widely used as components of cosmetic compositions and use thereof in order to impart glossiness to hair and the like is known (e.g. see Patent Document 1). Additionally, methylphenylpolysiloxane, known by the INCI name "Phenyl trimethicone" is used widely in the field of cosmetic compositions as it can impart shine and luster to a cosmetic composition (see Patent Document 2). Furthermore, silicone compounds having phenyl groups are widely known as having high refractive indices and it is also known that, in the control of the refractive index, the refractive index can be raised by introducing a phenyl group as a substituent on a polysiloxane sidechain (e.g. see Non-Patent Documents 1 and 2). Additionally, Patent Document 3 describes a cosmetic composition having a superior feeling of sheerness and luster comprising an alkylphenylpolysiloxane, wherein a phenyl group content is not less than 50%, as an essential component.

However, while the feeling of sheerness and the refractive index of a silicone resin having a phenyl group is superior, viscosity adjustment thereof is difficult and it is not possible to maintain the overall refractive index of the composition when diluted using an ordinary silicone oil to 1.50 or greater (more preferably from 1.55 to 1.60). Thus, there is a problem in that the refractive index declines, which leads to insufficient luster of the cosmetic composition. On the other hand, while the refractive index of methylphenylpolysiloxane is superior, it is generally difficult to set the phenyl group substitution ratio to 50% or greater and easily produce a highly viscous methylphenylpolysiloxane such as one with a viscosity greater than 200 mPa·s. Furthermore, chain methylphenylpolysiloxanes do not have a three-dimensionally crosslinked structure and, therefore, have low viscosity, are prone to elute from cosmetic compositions. Moreover, when a chain methylphenylpolysiloxane is compounded alone, sufficient satisfaction cannot be obtained with regards to the imparting of lasting luster to the cosmetic composition and improvement in sensation during use.

Patent Document 4 describes an alkyl-phenyl silsesquioxane resin composition useful in personal care compositions and the like, which enhances the durability and retention of a powder agent after application. Patent Document 5 describes a cosmetic composition for the purpose of imparting luster and the like, the composition comprising a propylphenylsilsesquioxane resin having a weight average molecular weight of 2,000 to 30,000, a phenyl silicone or similar aromatic solvent, and optional cosolvent.

Compositions comprising these propylphenylsilsesquioxane resins have a high refractive index. However, while a certain degree of effects are displayed in imparting lasting luster to a cosmetic composition, there is a demand for further improvement in the appearance and sensation during use thereof. Furthermore, in such a composition, compatibility particularly with the propylphenylsilsesquioxane resin and the phenyl silicone is insufficient and, as a result, separation of the oil components is prone to occur. Thus, there is a problem in that a uniform composition cannot be easily obtained. Particularly, there is a problem in that the storage stability of a cosmetic composition comprising said component is insufficient. Moreover, there is another problem in that it is difficult to control the viscosity. Furthermore, in a system containing both silicone powder and phenyl silicone oil, while sensation during use is improved, there is a demand for further improvement with regards to appearance such as shine and brilliance and attaining a sufficient refractive index and feeling of sheerness. Additionally, satisfactory storage stability cannot be obtained.

In an effort to resolve these problems, the present applicant proposed the phenyl group-containing organopolysiloxane composition recited in Patent Document 6. The phenyl group-containing organopolysiloxane composition comprises: (A) a phenylsilsesquioxane resin having a weight average molecular weight within a range of 500 to 2,000 and at least 15 mol % of the siloxy units constituting the resin are the phenyl siloxy unit: ($C_6H_5SiO_{3/2}$); and (B) a phenyl group-containing organopolysiloxane that is liquid at 25° C. and that has a refractive index of 1.45 or greater, in predetermined ranges. With this phenyl group-containing organopolysiloxane composition, an overall refractive index of the composition is high, and the phenylsilsesquioxane resin and the phenyl group-containing organopolysiloxane are uniformly miscible with each other and, therefore, compounding stability in a cosmetic composition and handling are superior and the viscosity can be easily adjusted.

However, in these prior art documents, there is no recitation of a branched silicone-based oil agent such as the liquid aryl group-containing polyorganosiloxane of the present invention. Furthermore, structurally, with the $T^{Ph}$ type phenylsilsesquioxanes used in the Practical Examples and the like in Patent Documents 1 to 6, the content of the phenyl groups per one mole of Si atoms is not greater than 1.0. Moreover, there is no mention whatsoever of an aryl group-containing polyorganosiloxane in which it is preferable to set the content of T branch units to be 50 mol % or less. Furthermore, there is no specific recitation of a liquid aryl group-containing polyorganosiloxane in which the content of T-type arylsiloxy units is limited and the content of phenyl groups per one mole of Si atoms is greater than 1.0. Thus, there is no recitation or implication whatsoever regarding the existence of technical problems and the technical benefits of such an aryl group-containing polyorganosiloxane having superior stability in a composition when mixed with an oil agent, and being able to be stably compounded in a non-aqueous cosmetic composition without turbidity that accompanies hydrolysis occurring.

PRIOR ART DOCUMENTS

Patent Documents

Patent Document 1: Japanese Unexamined Patent Application Publication No. S-62-234012
Patent Document 2: Japanese Unexamined Patent Application Publication No. H-01-168607A
Patent Document 3: Japanese Unexamined Patent Application Publication No. H-07-089844A (Patent No. 3207030B)
Patent Document 4: Japanese Unexamined Patent Application Publication (Translation of PCT Application) No. 2007-535586A
Patent Document 5: Japanese Unexamined Patent Application Publication No. 2009-19033A
Patent Document 6: Japanese Unexamined Patent Application Publication No. 2011-136935A
Non-Patent Document 1: "Personal Care Silicone No. Y517"; Dow Corning Toray Catalog, p. 13; published Feb. 1, 2009
Non-Patent Document 2: "Silicone Handbook", p. 404; Kunio ITO; published by The Nikkan Kogyo Shimbun., Ltd.

SUMMARY OF THE INVENTION

Technical Problem

The present inventors discovered new technical problems to be resolved in the high refractive index silicone resin composition having a high phenyl content described in Patent Document 6. In cases when mixed with an oil agent, $T^{Ph}$ type phenylsilsesquioxanes have problems such as being prone to hydrolysis, becoming turbid over time, and lacking stability as a cosmetic raw material or cosmetic product. Particularly, the inclusion of water that is a cause of white turbidness may negatively affect the stability and formulation of a nonaqueous cosmetic composition. Additionally, the present inventors discovered that while compatibility between the oil agent and the oleophilic component and compounding stability were generally superior in the high refractive index silicone resin composition having a high phenyl content described in Patent Document 6, depending on the formulation, there was room for improvement of compatibility and compounding stability for organic UV absorbers and similar oleophilic components, particularly those that have poor solubility and poor compatibility. Furthermore, the present inventors discovered that, while a conventional silicone-based oil agent having a high phenyl content has a superior feeling of sheerness, there was room for improvement in attaining a makeup finish with depth such as to achieve a taught and moist texture of the lips or skin. Moreover, the present inventors discovered that with such an oil agent, makeup was prone to running, and there was room for improvement in the durability of cosmetic effects. The present inventors also discovered that the hair cosmetic composition, comprising an ingredient that imparted luster to hair, was prone to lead a frizz after using thereof.

The present invention was created to solve the problems described above. An object of the present invention is to provide a novel liquid aryl group-containing polyorganosiloxane having, compared to conventional T phenyl resins (phenylsilsesquioxane), alkyl-phenyl silsesquioxane resin compositions, and the like, superior compatibility with an oil agent or an oleophilic component and, furthermore, when mixed with an oil agent, can be stably compounded in a non-aqueous cosmetic composition without turbidity that accompanies hydrolysis occurring when stored for an extended period of time, and also imparting good frizz control benefit to human hair with its shinny and luster appearance; a composition comprising an oil agent comprising the novel liquid aryl group-containing polyorganosiloxane and a high refractive index product; a cosmetic composition comprising the novel liquid aryl group-containing polyorganosiloxane; and a method for producing the novel liquid aryl group-containing polyorganosiloxane.

Solution to Problem

As a result of diligent research, the present inventors discovered that the problems described above could be solved by: A liquid aryl group-containing polyorganosiloxane comprising an arylsiloxy unit represented by $RSiO_{3/2}$ (wherein R is an aryl group), wherein: the arylsiloxy unit constitutes from 20 to 50 mol % of all the siloxy units constituting the polymer, and a number of moles of aryl groups per 1 mole of Si atoms in the molecule, on average, is within a range of 1.20 to 1.65; and a method for producing the liquid aryl group-containing polyorganosiloxane. Thus, the present invention was completed. Particularly, the present inventors discovered that the problems described above could be more favorably solved by a liquid aryl group-containing polyorganosiloxane comprising specific siloxane units, where an average molecular weight thereof is in a range from 500 to 2,000. Thus, the present invention was completed.

Additionally, the present inventors discovered that the problems described above could be more favorably solved by an aryl group-containing polyorganosiloxane composition comprising: (A) the liquid aryl group-containing polyorganosiloxane, and
(B) an oil agent (however, not the component (A)), wherein an overall refractive index of the composition is not less than 1.45, and an overall viscosity at 25° C. of the composition is in a range of 100 to 100,000 mPa·s; a cosmetic composition comprising the liquid aryl group-containing polyorganosiloxane or a composition thereof; and particularly, a cosmetic composition further comprising: (C) at least one type of oleophilic cosmetic raw material. Thus, the present invention was completed.

That is to say, the aforementioned object is attained by the following:

[1] A liquid aryl group-containing polyorganosiloxane comprising an arylsiloxy unit represented by RSiO$_{3/2}$ (wherein R is an aryl group), wherein: the arylsiloxy unit constitutes from 20 to 50 mol % of all the siloxy units constituting the polymer, and an average number of moles of aryl groups per one mole of Si atoms in the molecule is within a range of 1.20 to 1.65.

[2] The liquid aryl group-containing polyorganosiloxane described in [1], represented by the following average composition formula (1):

Average composition formula (1):

$$(R^1R^2R^3SiO_{1/2})a(R^4R^5SiO_{2/2})b(RSiO_{3/2})c(R'SiO_{3/2})d(SiO_{4/2})e \quad (1)$$

In this formula, $R^1$ to $R^5$ are each independently a monovalent organic group or a hydrogen atom, R is an aryl group, R' is a hydrogen atom or a monovalent organic group other than an aryl group, 0.20≤c≤0.50, a+b+c+d+e=1.0, a portion or all of $R^1$ to $R^5$ are aryl groups, and an average number of moles of aryl groups per one mole of Si atoms in the molecule of a to e is in a range of 1.20 to 1.65.

[2-1] The liquid aryl group-containing polyorganosiloxane described in [2], wherein the aryl groups is a phenyl group or a naphthyl group and, furthermore, 0.10≤b≤0.40.

[3] The liquid aryl group-containing polyorganosiloxane described in [1] or [2], represented by the following average composition formula (1-1):

Average composition formula (1-1):

$$(R^4{}_2R^6SiO_{1/2})a'(R^4R^7SiO_{2/2})b'(R^4SiO_{3/2})c' \quad (1\text{-}1)$$

In this formula, $R^4$ is a phenyl group or a naphthyl group, $R^6$ and $R^7$ are each independently a monovalent organic group or a hydrogen atom, 0.10≤b'≤0.40 and 0.20≤c'≤0.50, a'+b'+c'=1.0, and a number of moles of phenyl groups or a naphthyl groups per 1 mole of Si atoms in the molecule of a' to c' is, on average, in a range of 1.20 to 1.65.

[3-1] The liquid aryl group-containing polyorganosiloxane described in any one of [1] to [3], represented by the average composition formula (1-2) or (1-3) below:

Average composition formula (1-2):

$$(Ph_2MeSiO_{1/2})a''(PhMeSiO_{2/2})b''(PhSiO_{3/2})c'' \quad (1\text{-}2)$$

Average composition formula (1-3):

$$(Ph_2MeSiO_{1/2})a''(PhMeSiO_{2/2})b''(NpSiO_{3/2})c'' \quad (1\text{-}3)$$

In these formulae, Ph is a phenyl group, Me is a methyl group, Np is a naphthyl group, 0.10≤b'≤0.40, 0.20≤c''≤0.50, a''+b''+c''=1.0, and a'' to c'' have relationships such that [2×a''+b''+c'']/[a''+b''+c'']=1.20 to 1.65 is satisfied.

[4] The liquid aryl group-containing polyorganosiloxane described in any one of [1] to [3], wherein a refractive index is not less than 1.50, and weight average molecular weight as measured by gel permeation chromatography (GPC) is in a range of 500 to 2,000.

[4-1] The liquid aryl group-containing polyorganosiloxane described in any one of [1] to [3], wherein the refractive index is from 1.55 to 1.65, and the weight average molecular weight as measured by gel permeation chromatography (GPC) is in a range of 550 to 1,750.

[5] An aryl group-containing polyorganosiloxane composition comprising: (A) a liquid aryl group-containing polyorganosiloxane described in any one of [1] to [4], and (B) an oil agent (however, not the component (A)), wherein an overall refractive index of the composition is not less than 1.45, and an overall viscosity at 25° C. of the composition is in a range of 100 to 100,000 mPa·s.

[6] The aryl group-containing polyorganosiloxane composition described in [5], wherein the component (B) is a phenyl group-containing organopolysiloxane represented by structural formula (2-1) or structural formula (2-2) below:

Structural formulae:

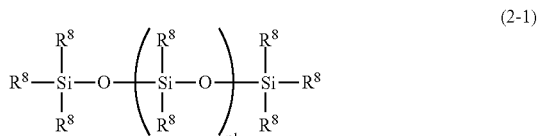

(2-1)

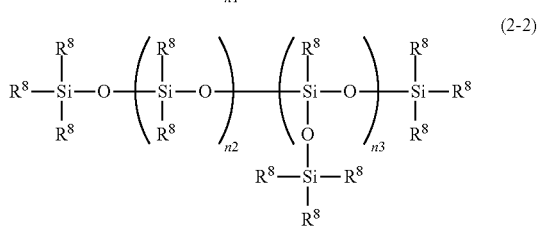

(2-2)

In these formulae, $R^8$ is a group selected from a phenyl group, an aralkyl group, a hydrogen atom, a hydroxyl group, or a fluorinated alkyl group or an alkyl group having from 1 to 20 carbons and, in terms of molar ratio, at least 50% of the $R^8$ moieties are phenyl groups; n1 or n2 is a number in a range of 0 to 1,000; and n3 is a number in a range of 1 to 1,000.

[6-1] The aryl group-containing polyorganosiloxane composition described in [5] or [6], wherein the component (B) is a dimethyltetraphenyldisiloxane or a trimethylpentaphenyltrisiloxane.

[7] A cosmetic composition comprising a liquid aryl group-containing polyorganosiloxane described in any one of [1] to [4].

[8] A cosmetic composition comprising a liquid aryl group-containing polyorganosiloxane composition described in [5] or [6].

[9] The cosmetic composition described in [7] or [8], further comprising: (C) one or more types of oleophilic cosmetic raw material.

[9-1] The cosmetic composition described in [9], wherein the component (C) is (C1) an organic UV absorber.

[10] The cosmetic composition described in any one of [7] to [9-1] that is a makeup cosmetic composition, a hair cosmetic composition, or a skin cosmetic composition.

[11] A method for producing a liquid aryl group-containing polyorganosiloxane described in any one of [1] to [4] comprising: a step (I) of mixing (A-1) at least one type of organosilicon compound selected from an aryl group-containing polyorganosiloxane that is solid at 25° C. and that comprises an arylsiloxy unit represented by RSiO$_{3/2}$ (wherein R is an aryl group), wherein the arylsiloxy unit constitutes not less than 50 mol % of all the siloxy units constituting the polymer; an organosilane represented by RSiX$_{3-n4}$(OR$^9$)$_{n4}$ (wherein R is an aryl group, X is a halogen atom, $R^9$ are each independently a hydrogen atom or an alkyl group having from 1 to 6 carbons, and n4 is a number within a range of 0 to 3); and a condensation reaction product of said organosilane;

(A-2) an aryl group-containing organopolysiloxane oligomer represented by structural formula (3) below:

Structural Formula (3):

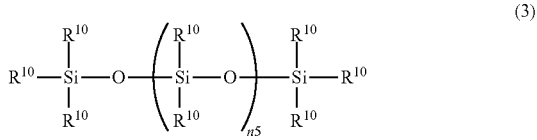

(3)

In this formula, $R^{10}$ are each independently a monovalent organic group and, in terms of molar ratio, at least 50% of the $R^{10}$ moieties are aryl groups, and n5 is a number in a range of 0 to 10; and (A-3) a catalyst; and
a step (II) of equilibration reaction of the mixture obtained in step (I).
[11-1] The method for producing the liquid aryl group-containing polyorganosiloxane described in [11], wherein the component (A-1) is a solid phenylsilsesquioxane constituted essentially by $PhSiO_{3/2}$ units, the component (A-2) is a phenyl group-containing organopolysiloxane oligomer represented by structural formula (3-1);

Structural Formula (3-1):

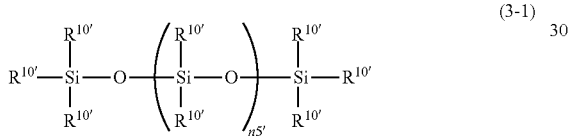

(3-1)

In this formula, $R^{10'}$ are each independently a monovalent organic group and, in terms of molar ratio, at least 50% of the $R^{10'}$ moieties are phenyl groups, and n5' is a number in a range of 0 to 1; and
the component (A-3) is an alkaline catalyst.
[11-2] The method for producing the liquid aryl group-containing polyorganosiloxane described in [11] or [11-1], wherein: the step (I) is a step of mixing the components (A-1) to (A-3) and (A-4) a solvent;
the step (II) is a step of equilibration reaction of the mixture obtained in step (I) while heating and stirring at a temperature in a range of 80° C. to 200° C.; and
further comprises a step after the step (II) of removing the solvent.

Advantageous Effects of Invention

According to the present invention, a novel liquid aryl group-containing polyorganosiloxane, a composition having a high refractive index comprising an oil agent and the novel liquid aryl group-containing polyorganosiloxane, a cosmetic composition comprising the novel liquid aryl group-containing polyorganosiloxane and a method for producing the novel liquid aryl group-containing polyorganosiloxane can be provided. Compared to conventional T phenyl resins (phenylsilsesquioxane), alkyl-phenyl silsesquioxane resin compositions, and the like, these compounds have superior compatibility with an oil agent or an oleophilic component and, furthermore, when mixed with an oil agent, can be stably compounded in a non-aqueous cosmetic composition without turbidity that accompanies hydrolysis occurring when stored for an extended period of time. Moreover, makeup finish with depth can be attained using a small amount, makeup running does not easily occur, and the durability of cosmetic effects is superior. Furthermore, the novel liquid aryl group-containing polyorganosiloxane according to the present invention can be suitably compounded in a makeup cosmetic composition, a hair cosmetic composition, or a skin cosmetic composition, and various cosmetic compositions can be provided having superior sensation during use, appearance, and color. In hair cosmetic composition combined with the novel liquid aryl group-containing organopolysiloxane, the hair cosmetic composition imparts excellent frizz control benefit to human hair. Additionally, the novel liquid aryl group-containing polyorganosiloxane according to the present invention has a higher refractive index than conventionally known silicone-based oil agents and, therefore, when used in combination with titanium oxide or a similar high refractive index powder, a difference between the refractive indices of the powder and the oil agent will be small. As a result, the feeling of sheerness on the skin is superior and white flaking on the skin can be reduced and, therefore, there is an advantage in that even if cosmetic film accumulates in wrinkled portions, said film will not be noticeable and a natural appearance can be obtained. On the other hand, in cases where combined with silicone elastomer particles having a relatively low refractive index, the difference between the refractive indices of the powder and the oil agent will be sufficiently great. Therefore, compared to conventional cosmetic composition-use oil agents, there is an advantage in that superior soft focus effects can be obtained.

DETAILED DESCRIPTION OF THE PREFERRED EMBODIMENT

Figure 1:
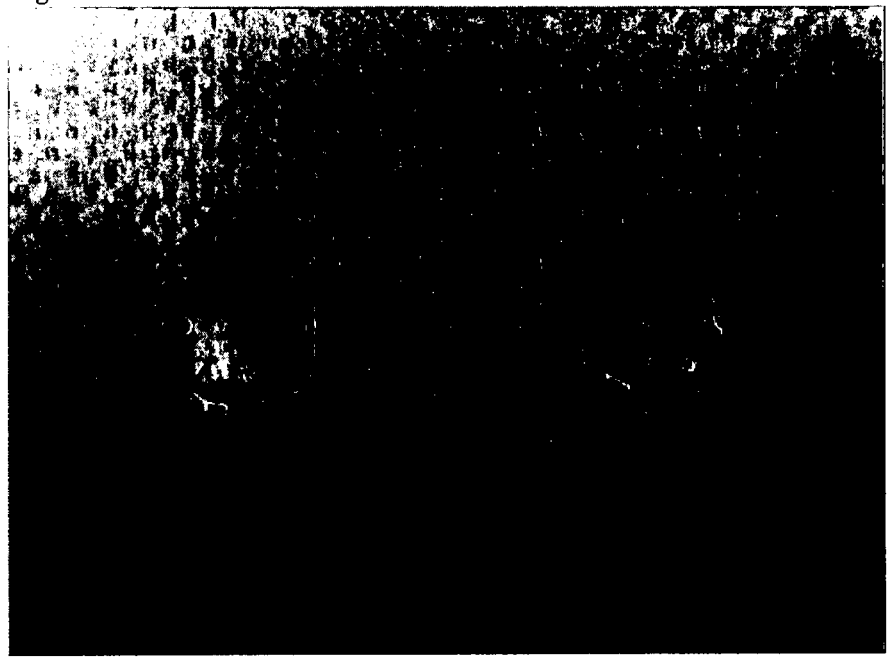
FIG. 1 depicts the appearance of samples of 0.1 g of trimethylpentaphenyltrisiloxane (left) and a Practical Example (right, sample No. 4), immediately after dropping on collagen film.

A detailed description of the liquid aryl group-containing polyorganosiloxane of the present invention is given below.

The liquid aryl group-containing polyorganosiloxane according to the present invention comprises an arylsiloxy unit represented by $RSiO_{3/2}$ (wherein R is an aryl group), wherein: the arylsiloxy unit constitutes from 20 to 50 mol % of all the siloxy units constituting the polymer, and an average number of moles of aryl groups per one mole of Si atoms in the molecule is within a range of 1.20 to 1.65.

The liquid aryl group-containing polyorganosiloxane according to the present invention is liquid at room temperature (25° C.), has fluidity, and a kinetic viscosity thereof is preferably in a range from 500 to 50,000 mPa·s, more preferably in a range from 750 to 20,000 mPa·s, and even more preferably in a range from 850 to 15,000 mPa·s. As described hereinafter, an average molecular weight of the liquid aryl group-containing polyorganosiloxane according to the present invention is preferably not more than 2,000, and the liquid aryl group-containing polyorganosiloxane is preferably a transparent liquid having a viscosity within the range described above when in a liquid state.

The aryl group (R moiety) is a component that imparts a high refractive index of not less than 1.50 to the liquid aryl group-containing polyorganosiloxane according to the present invention. Examples thereof include a phenyl group, a naphthyl group, an anthracenyl group, a phenanthrenyl group, and similar aryl groups having from 6 to 14 carbons; and functional groups in which a portion or all of the hydrogen atoms of these aryl groups are substituted with chlorine, fluorine, or a similar halogen atom. From an industrial viewpoint, a phenyl group or a naphthyl group is preferable, and of naphthyl groups, a 1-naphthyl group is particularly preferable. Additionally, a content of the phenyl group or the naphthyl group per one mole of Si atoms in the molecule must be in a range from 1.20 to 1.65 in terms of the average number of moles of aryl groups and, in order to impart the high refractive index of not less than 1.50, is preferably in a range from 1.30 to 1.65 and most preferably in a range from 1.35 to 1.55 in terms of the average number of moles of aryl groups per one mole of Si atoms in the molecule. From a technical perspective, production will be difficult if the number of moles of the aryl group exceeds the upper limit described above. Additionally, if the number of moles is less than the lower limit described above, the refractive index will be insufficient, and the resulting product will be unsuitable as a highly refractive and highly transparent cosmetic raw material.

Furthermore, with the liquid aryl group-containing polyorganosiloxane of the present invention, a content of the arylsiloxy unit represented by $RSiO_{3/2}$ (wherein R is an aryl group) is in a range from 20 to 50 mol % of all the siloxy units constituting the polymer. If the amount of $RSiO_{3/2}$ units exceeds the upper limit described above, fluidity as an oil agent will decline and handling will be negatively affected. On the other hand, it is not preferable that the amount of the $RSiO_{3/2}$ units is less than the lower limit described above, because the viscosity of the resulting product will be excessively low. As a result, compounding stability, in cases where compounded in a cosmetic composition or the like, will be negatively affected, and appearance when applying a makeup product will lack sufficient depth, makeup running will be prone to occur, the durability of cosmetic effects will decline, and the frizz control benefit will be impaired.

Preferably, the liquid aryl group-containing polyorganosiloxane of the present invention comprises an arbitrary combination of triorganosiloxy units (M units), diorganosiloxy units (D units), monoorganosiloxy units (T units), and tetrafunctional siloxy units (Q units) represented by average composition formula (1) below.

Average composition formula (1):

$$(R^1R^2R^3SiO_{1/2})a(R^4R^5SiO_{2/2})b(RSiO_{3/2})c(R'SiO_{3/2})d(SiO_{4/2})e \quad (1)$$

In this formula, $R^1$ to $R^5$ are each independently a monovalent organic group or a hydrogen atom, R is an aryl group, R' is a hydrogen atom or a monovalent organic group other than an aryl group, $0.20 \le c \le 0.50$, $a+b+c+d+e=1.0$, a portion or all of $R^1$ to $R^5$ are aryl groups, and "a" to "e" are numbers such that an average number of moles of aryl groups per one mole of Si atoms in the molecule is in a range of 1.20 to 1.65. Preferably, the liquid aryl group-containing polyorganosiloxane of the present invention comprises diorganosiloxy units (D units) represented by $R^4R^5SiO_{2/2}$; preferably $0.10 \le b \le 0.40$ and more preferably $0.15 \le b \le 0.30$. Likewise, a sum of the other M units, T units, and Q units $(a+d+e)$ is such that $0.10 \le (a+d+e) \le 0.70$ and particularly preferably such that $0.20 \le (a+d+e) \le 0.65$.

While not limited thereto, specific examples of the $R^1$ to $R^5$ moieties include hydrogen atoms, alkyl groups having from 1 to 8 carbons, alkenyl groups having from 2 to 10 carbons, fluoroalkyl groups, and similar halogen-substituted alkyl groups; long chain alkyl groups having from 9 to 30 carbons, phenyl groups, naphthyl groups, hydroxyl groups, and the like. From an industrial viewpoint, the $R^1$ to $R^5$ moieties are preferably methyl groups, vinyl groups, phenyl groups, naphthyl groups, or hydroxyl groups. Here, $R^1$ and $R^2$ are preferably aryl groups, and particularly preferably are phenyl groups. $R^3$ is preferably a methyl group, a vinyl group, or a hydroxyl group. $R^4$ is preferably an aryl group, and particularly preferably is a phenyl group. $R^5$ is preferably an aryl group, and particularly preferably is a phenyl group.

The R moiety is an aryl group, and preferably is a phenyl group or a naphthyl group (1-naphthyl group), synonymous with those described above.

The R' moiety is a monovalent organic group other than an aryl group or a hydrogen atom. While not limited thereto, specific examples of the R' moiety include a hydrogen atom, alkyl groups having from 1 to 8 carbons, alkenyl groups having from 2 to 10 carbons, fluoroalkyl groups, and similar halogen-substituted alkyl groups; long chain alkyl groups having from 9 to 30 carbons, hydroxyl groups, and the like. From an industrial viewpoint, the R' moiety is preferably a methyl group, a vinyl group, or a hydroxyl group.

In the liquid aryl group-containing polyorganosiloxane of the present invention, the content of the arylsiloxy unit represented by $RSiO_{3/2}$ (wherein R is an aryl group) is in the range from 20 to 50 mol % of all the siloxy units constituting the polymer. Therefore, in the average composition formula (1), when the sum of the siloxane units $(a+b+c+d+e)$ is equal to 1.0, "c" (i.e. the number of arylsiloxy units represented by $RSiO_{3/2}$ (wherein R is an aryl group)) must be such that $0.20 \le c \le 0.50$. Additionally, in the liquid aryl group-containing polyorganosiloxane of the present invention, the average number of moles of aryl groups per one mole of Si atoms in the molecule is in a range of 1.20 to 1.65. Therefore, in cases where "a" to "e" comprise functional groups corresponding to the aryl groups of the $R^1$ to $R^5$ moieties, in consideration of said number of aryl groups, the average number of moles of aryl groups per one mole of Si atoms in the molecule is in a range from 1.20 to 1.65. For example, in cases where the $R^1$ to $R^5$ moieties in the molecule are functional groups corresponding to all of the aryl groups, "a" to "e" are numbers in a range such that $(3a+2b+c)/(a+b+c+d+e)=1.20$ to 1.65. Additionally, in cases where the $R^1$ to $R^5$ moieties in the molecule are functional groups not corresponding to all of the aryl groups, "a" to "e" are numbers in a range such that $c/(a+b+$ c+d+e)=1.20 to 1.65. However, in either case, "c" must satisfy 0.20≤c≤0.50. Note that "a" to "e" are preferably numbers such that the average number of moles of aryl groups per one mole of Si atoms is in a range from 1.30 to 1.65 and most preferably in a range from 1.35 to 1.55.

From the perspective of achieving a high refractive index, preferable examples of the liquid aryl group-containing polyorganosiloxane of the present invention include those comprising diarylorganosiloxy units ($M^{Aryl(2)}$ units), arylorganosiloxy units ($D^{Aryl}$ units), and arylsiloxy units ($T^{Aryl}$ units) represented by average composition formula (1-1) below.

Average composition formula (1-1):

$$(R^A{}_2R^6SiO_{1/2})a'(R^AR^7SiO_{2/2})b'(R^ASiO_{3/2})c' \qquad (1\text{-}1)$$

In this formula, $R^A$ is a phenyl group or a naphthyl group, $R^6$ and $R^7$ are each independently a monovalent organic group or a hydrogen atom, 0.20≤c'≤0.50, a'+b'+c'=1.0, and an average number of moles of phenyl groups or a naphthyl groups per one mole of Si atoms in the molecule of a' to c' is in a range of 1.20 to 1.65. Preferably, b' is a number in a range such that 0.10≤b'≤0.40, and more preferably such that 0.15≤b'≤0.30.

Specific examples of the $R^6$ and $R^7$ moieties include hydrogen atoms, alkyl groups having from 1 to 8 carbons, alkenyl groups having from 2 to 10 carbons, fluoroalkyl groups, and similar halogen-substituted alkyl groups; long chain alkyl groups having from 9 to 30 carbons, phenyl groups, naphthyl groups, hydroxyl groups, and the like. From an industrial viewpoint, of these, methyl groups, vinyl groups, phenyl groups, naphthyl groups, or hydroxyl groups are preferable.

From the perspective of industrial production, the $R^6$ and $R^7$ moieties are most preferably all methyl groups. In this case, the liquid aryl group-containing polyorganosiloxane of the present invention is represented by average composition formula (1-2) or (1-3) below.

Average composition formula (1-2):

$$(Ph_2MeSiO_{1/2})a''(PhMeSiO_{2/2})b''(PhSiO_{3/2})c'' \qquad (1\text{-}2)$$

Average composition formula (1-3):

$$(Ph_2MeSiO_{1/2})a''(PhMeSiO_{2/2})b''(NpSiO_{3/2})c'' \qquad (1\text{-}3)$$

In these formulae, Ph is a phenyl group, Me is a methyl group, Np is a naphthyl group, 0.10≤b''≤0.40, 0.20≤c''≤0.50, a''+b''+c''=1.0, and a'' to c'' have relationships such that [2×a''+b''+c'']/[a''+b''+c'']=1.20 to 1.65 is satisfied.

Note that in average composition formulae (1-1) and (1-2), a' to c' and a'' to c'' are preferably numbers such that the average number of moles of aryl groups per one mole of Si atoms is in a range from 1.30 to 1.65 and most preferably in a range from 1.35 to 1.55.

When compounded in a cosmetic composition, it is preferable that the liquid aryl group-containing polyorganosiloxane has a feeling of sheerness, and can impart lasting shine, brilliance, and luster when used. Therefore the liquid aryl group-containing polyorganosiloxane according to the present invention preferably has a refractive index of not less than 1.50, particularly preferably in a range from 1.50 to 1.65, and most preferably in a range from 1.55 to 1.65

Compared with known T phenyl resins (phenylsilsesquioxane), alkyl-phenylsilsesquioxane resin compositions, and the like, the liquid aryl group-containing polyorganosiloxane according to the present invention has a significantly lower viscosity and lower molecular weight, and provides a technical benefit in that a single product having superior handling/workability and compounding stability as an "oil agent" with a high refractive index can be obtained. Specifically, a weight average molecular weight as measured by gel permeation chromatography (GPC) of the liquid aryl group-containing polyorganosiloxane according to the present invention is preferably not more than 2,000, more preferably in a range from 500 to 2,000, even more preferably in a range from 550 to 1,750, and most preferably in a range from 600 to 1,000. As a result of the low degree of polymerization, affinity and compatibility with other oil agents and oleophilic components is further improved. Moreover, it goes without saying that the overall refractive index of the composition can easily be made high. Additionally, handling/workability and compounding stability are significantly improved.

Such a liquid aryl group-containing polyorganosiloxane is not specifically described in the prior art and, compared to known T phenyl resins (phenylsilsesquioxane), alkyl-phenylsilsesquioxane resin compositions, and the like, have superior compatibility with oil agents and oleophilic components. Furthermore, in cases where mixed with an oil agent, a significant technical benefit can be provided in that the liquid aryl group-containing polyorganosiloxane can be stably compounded in a non-aqueous cosmetic composition without turbidity that accompanies hydrolysis occurring when stored for an extended period of time.

Additionally, compared with known phenylpolysiloxanes such as trimethylpentaphenyltrisiloxane and the like, the liquid aryl group-containing polyorganosiloxane of the present invention has the benefits of providing superior durability of cosmetic effects on the skin and maintaining lasting shine, brilliance, and luster of the cosmetic composition. Specifically, in cases where applied to the skin as an oil agent, makeup running that accompanies the diffusing or penetration of the oil agent on the skin does not easily occur, and cosmetic effects are maintained over an extended period of time. As a result, because the liquid aryl group-containing polyorganosiloxane of the present invention is not prone to diffusing on the skin, the desired depth when applied and a rich finish having shine and luster with a feeling of sheerness can be attained. Moreover, makeup touchups are not necessary over an extended period of time. Particularly, benefits are provided in that even with a small amount of the liquid aryl group-containing polyorganosiloxane of the present invention, makeup can be applied to the lips and around the eyes that gives an impression of depth, makeup running overall and at pinpoint locations is prevented, and a beautiful makeup finish can be maintained as it was immediately after completion.

As a result, the liquid aryl group-containing polyorganosiloxane of the present invention is particularly useful as a cosmetic composition, specifically as a raw material of a makeup cosmetic composition having luster. That is, the liquid aryl group-containing polyorganosiloxane of the present invention is particularly useful as a raw material of a makeup cosmetic composition by which a finish with depth having superior shine, luster, and tactile sensation can be achieved with a small amount, makeup running does not easily occur, and that has superior durability of cosmetic effects.

Furthermore, the refractive index of the liquid aryl group-containing polyorganosiloxane of the present invention is higher compared to that of other oil-based components and affinity with powders or coloring agents is superior. Therefore, variations in color of a coloring agent that occur when compounding with other components is suppressed by premixing the liquid aryl group-containing polyorganosiloxane with the coloring agent and coating this mixture on a surface. As a result, even when preparing a cosmetic composition such as lipstick, a lip gloss, eye shadow, blush, or the like, there is a benefit in that coloration can be easily and simply adjusted.

Additionally, the liquid aryl group-containing polyorganosiloxane of the present invention can be compounded in skin cosmetic compositions and hair cosmetic compositions and, has the benefit of providing superior sensation during use such as compatibility with the skin and the like, particularly when compounded in skin cosmetic compositions. Likewise, the novel liquid aryl group-containing polyorganosiloxane according to the present invention has a higher refractive index than conventionally known silicone-based oil agents and, therefore, when used in combination with titanium oxide or a similar high refractive index powder, there are benefits in that the feeling of sheerness on the skin is superior, white flaking does not occur, and a natural finish is achieved due to the difference between the refractive indices of the powder and the oil agent is small. On the other hand, in cases where combined with silicone elastomer particles for the purpose of achieving soft focus effects, the difference between the refractive indices of the powder and the oil agent will be sufficiently great. Therefore, compared to conventional cosmetic composition-use oil agents, there is an advantage in that superior soft focus effects can be obtained. Thus, the liquid aryl group-containing polyorganosiloxane according to the present invention is useful in that various advantageous effects can be provided depending on the desired cosmetic effects and combinations with the powder to be used. Additionally, In hair cosmetic composition combined with the novel liquid aryl group-containing organopolysiloxane, the hair cosmetic composition imparts excellent frizz control benefit to human hair.

From an industrial perspective, the liquid aryl group-containing polyorganosiloxane according to the present invention can be easily produced via the method described below.

Specifically, the liquid aryl group-containing polyorganosiloxane according to the present invention can be obtained via a method for production comprising: (I) a step of uniformly mixing components (A-1) to (A-3) and optionally a component (A-4) shown below;
(II) a step of equilibration reaction of the mixture obtained in step (I) while heating and stirring; and
an optional step of removing the solvent.
(A-1) At least one type of organosilicon compound selected from an aryl group-containing polyorganosiloxane that is solid at 25° C. and that comprises an arylsiloxy unit represented by $RSiO_{3/2}$ (wherein R is an aryl group), wherein the arylsiloxy unit constitutes not less than 50 mol % of all the siloxy units constituting the polymer; an organosilane represented by $RSiX_{3-n4}(OR^9)_{n4}$ (wherein R is an aryl group, X is a halogen atom, $R^9$ are each independently a hydrogen atom or an alkyl group having from 1 to 6 carbons, and n4 is a number within a range of 0 to 3); and a hydrolysis/condensation reaction product of said organosilane.
(A-2) an aryl group-containing organopolysiloxane oligomer represented by structural formula (3) below:

Structural Formula (3):

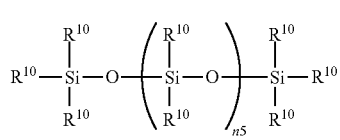

(3)

In this formula, $R^{10}$ are each independently a monovalent organic group and, in terms of molar ratio, at least 50% of the $R^{10}$ moieties are aryl groups, and n5 is a number in a range of 0 to 10.
(A-3) A catalyst.
(A-4) A solvent.

The component (A-1) is at least one type of organosilicon compound selected from the aryl group-containing polyorganosiloxane that comprises an arylsiloxy unit represented by $RSiO_{3/2}$ (wherein R is an aryl group), wherein the arylsiloxy unit constitutes not less than 50 mol % of all the siloxy units; the organosilane represented by $RSiX_{3-n4}(OR^9)_{n4}$ (wherein R is an aryl group, X is a halogen atom, $R^9$ are each independently a hydrogen atom or an alkyl group having from 1 to 6 carbons, and n4 is a number within a range of 0 to 3); and a hydrolysis/condensation reaction product of said organosilane. Each of these is a raw material component that is introduced into the polymer of the liquid aryl group-containing polyorganosiloxane of the present invention as an arylsiloxy unit represented by $RSiO_{3/2}$ (wherein R is an aryl group).

Examples of the aryl group-containing polyorganosiloxane comprising the arylsiloxy units represented by $RSiO_{3/2}$ (wherein R is an aryl group) at an amount of not less than 50 mol % of all the siloxy units include a T type polyorganosiloxane resin consisting solely of arylsiloxy units (T units) represented by $RSiO_{3/2}$ (wherein R is an aryl group) and, a MDT type polyorganosiloxane resin that further comprises diorganosiloxy units (D units), monoorganosiloxy units (M units), and the like. Particularly, preferably from 90 to 100 mol % of all the siloxy units are the arylsiloxy unit, more preferably from 95 to 100 mol % are the arylsiloxy unit, and most preferably, the component (A-1) is a solid phenylsilsesquioxane in which 100 mol % of all the siloxy units are $PhSiO_{3/2}$ units (wherein Ph is a phenyl group). These are examples of solid phenylsilsesquioxanes, substantially consisting solely of the arylsiloxy unit.

Likewise, an organosilane represented by $RSiX_{3-n4}(OR^9)_{n4}$ (wherein R is an aryl group, X is a halogen atom, $R^9$ are each independently a hydrogen atom or an alkyl group having from 1 to 6 carbons, and n4 is a number within a range of 0 to 3); or a condensation reaction product of said organosilane can be used as the component (A-1). Particularly, when n4 is a number other than 3, the component (A-1) is preferably a hydrolysis/condensation reaction product that is condensed via hydrolysis of a halogen atom X and water.

The organosilane represented by $RSiX_{3-n4}(OR^9)_{n4}$ is a component that provides a condensation reaction product comprising the arylsiloxy units (T units) represented by $RSiO_{3/2}$ (wherein R is an aryl group) via a hydrolysis or condensation reaction. As described above, R is preferably a phenyl group or a naphthyl group. Additionally, X is preferably chlorine (Cl) and the group represented by $OR^9$ is preferably a hydroxyl group, or a methoxy group, an ethoxy group, or similar alkoxy group. n4 is a number in a range from 0 to 3. For example, when X is a chlorine atom and the group represented by $OR^9$ is a methoxy group, if n4 is 0, the component (A-1) is an aryltrichlorosilane and, if n4 is 3, the component (A-1) is an aryltrimethoxysilane. Note that in cases other than when n4 is 3, water is preferably added to the reaction system for the purpose of hydrolyzing the organohalosilane. While not limited thereto, examples of the organosilane represented by the formula shown above include phenyltrichlorosilane, phenylmethoxydichlorosilane, phenyldimethoxychlorosilane, phenyltrimethoxysilane, naphthyltrichlorosilane, naphthylmethoxydichlorosilane, naphthyldimethoxychlorosilane, and the like. One type or two or more types of these organosilanes may be used and are used in an amount such that the content of arylsiloxy units in the liquid aryl group-containing polyorganosiloxane after reaction with the component (A-2) (described hereinafter) is from 20 to 50 mol % of all the siloxy units. Furthermore, these organosilanes may be condensation reaction products of condensed organosilanes that has been condensed alone or in conjunction with hydrolysis beforehand. Note that a condensation reaction product consisting only of the organosilane constitutes a T-type polyorganosiloxane resin. Here, when a hydrolysis/condensation reaction product in which n4 is a number other than 3 is used as the component (A-1), hydrochloric acid and similar acidic substances are produced as byproducts. Therefore, equilibration can be performed as-is using the acidic substance, or the hydrolysis/condensation reaction product can be used as a raw material in the equilibration reaction after neutralizing (beforehand) using a basic substance or the like. However, an alkaline catalyst is preferably used in the equilibration reaction of the liquid aryl group-containing polyorganosiloxane of the present invention and, therefore, a condensation product that has been neutralized beforehand via a condensation reaction is preferably used as the component (A-1).

These components (A-1), that is, the organosilane represented by $RSiX_{3-n4}(OR^9)_{n4}$ and the aryl group-containing polyorganosiloxane that comprises the arylsiloxy unit represented by $RSiO_{3/2}$ (wherein R is an aryl group), wherein the arylsiloxy unit constitutes not less than 50 mol % of all the siloxy units can both be used in the method of producing the present invention without limitation. Moreover, the component (A-1) may be a mixture of the organosilane and the aryl group-containing polyorganosiloxane. Additionally, as necessary, the component (A-1) can be dissolved in the aryl group-containing organopolysiloxane oligomer component (A-2) (described hereinafter) or in the optional solvent (component (A-4)) and added to the reaction system.

The component (A-2) is the aryl group-containing organopolysiloxane oligomer represented by the structural formula (3) above and is the primary component for regulating the reaction amount of the component (A-1) and adjusting the content of the arylsiloxy unit in the liquid aryl group-containing polyorganosiloxane according to the present invention to be from 20 to 50 mol % of all the siloxy units. The component (A-2) may be a single type or a mixture of two or more types.

In the structural formula (3), the $R^{10}$ moieties are each independently a monovalent organic group, specifically, an alkyl group having from 1 to 8 carbons, an alkenyl group having from 2 to 10 carbons, a fluoroalkyl group or similar halogen-substituted alkyl group, a long chain alkyl group having from 9 to 30 carbons, a phenyl group, or a naphthyl group. Moreover, at least 50% of the $R^{10}$ moieties, in terms of molar ratio, are aryl groups (phenyl groups or naphthyl groups). n1 is a number in a range from 0 to 10, preferably a number in a range from 0 to 5, and more preferably a number in a range from 0 to 1. Note that, from 50 to 90 mol % of the $R^{10}$ moieties are preferably aryl groups (phenyl groups or naphthyl groups).

While not limited thereto, specific examples of the component (A-2) include the following phenyltetrasiloxane, phenyltrisiloxane, and phenyldisiloxane. Most preferably, the component (A-2) of the present invention is a trimethylpentaphenyltrisiloxane or a dimethyltetraphenyldisiloxane.

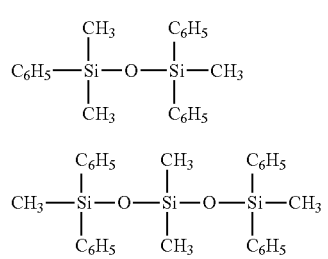

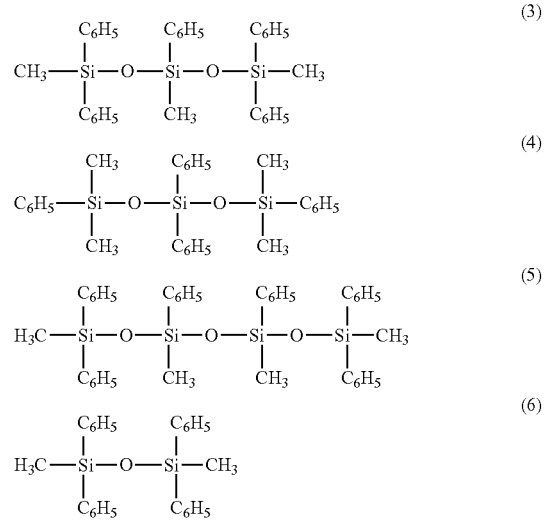

The component (A-3) is a catalyst of the components described above and any acidic catalyst or alkaline catalyst can be used. However, an alkaline catalyst is preferable and an alkali metal hydroxide catalyst is particularly preferable. Specific examples thereof include potassium hydroxide, sodium hydroxide, lithium hydroxide, rubidium hydroxide, cesium hydroxide, and similar hydroxides of alkali metals; sodium-t-butoxide, potassium-t-butoxide, cesium-t-butoxide, and similar alkoxides of alkali metals; and sodium silanolate compounds, potassium silanolate compounds, cesium silanolate compounds, and similar silanol compounds of alkali metals. Of these, cesium hydroxide is particularly preferable. A catalyst with a normal purity of not less than 90 wt. % is used. A content thereof can be appropriately selected based on the scale of the reaction and the desired rate of reaction but, generally, when a sum of the component (A-1) and the component (A-2) is 100 parts by weight, the content of the component (A-3) is in a range from 0.01 to 1.0 parts by weight, and preferably from 0.05 to 0.5 parts by weight.

The component (A-4) is a solvent, and can be used optionally based on the type of the component (A-1) and the usage amount of the component (A-2). Particularly, in cases where the component (A-1) is the aryl group-containing polyorganosiloxane substantially constituted solely by the arylsiloxy unit represented by $RSiO_{3/2}$ (wherein R is an aryl group), from the perspective of handling and the perspective of the reaction, that is, preventing separation of the resin-like silicone in the reaction, mixing with other components, and the like, the solvent is preferably used. Specific examples of usable organic solvents include toluene, xylene, and similar aromatic organic solvents; acetone, methyl isobutyl ketone, and similar ketone-based organic solvents; and hexane, heptane, octane, and similar aliphatic organic solvents. Of these, aromatic organic solvents are preferable. Additionally, it is preferable that such an organic solvent is compounded because removal of free water produced as a result of the condensation reaction when synthesizing, via azeotropic dehydration, from the resulting aryl group-containing polyorganosiloxane is easy. Additionally, an amount of the organic solvent used when producing the composition described above can be selected as desired but, when the sum of the component (A-1) and the component (A-2) is 100 parts by weight, the amount is in a range from 0 to 1,000 parts by weight and, from the perspective of facilitating the stripping process performed after the equilibration reaction, is preferably in a range from 10 to 200 parts by weight. In addition, by controlling the solid content concentration in the solvent, the balance state of the reaction system can be managed, the molecular weight of the resulting liquid aryl group-containing polyorganosiloxane can be controlled, and the molecular weight range of the product can be stabilized. As a result, from the perspective of industrial production, the inclusion of the organic solvent is useful in standardization (e.g. standardization of the molecular weight of the product and the like).

Mixing of the components (A-1) to (A-3) and the optional component (A-4) can be carried out using a paddle mixer or similar known mixing device or kneading device, and may be carried out in the reaction vessel. Additionally, optional components mixed in a separate container may be transferred to the reaction vessel.

In the equilibration reaction, the siloxane bonds of the component (A-1) and the component (A-2) disconnect and reconnect randomly and, as a result, the siloxane units in the organopolysiloxanes present in the reaction system are redistributed and, thus, the desired liquid aryl group-containing polyorganosiloxane according to the present invention is formed. The equilibration reaction is carried out by heating in the presence of the catalyst component (A-3).

Conditions of the equilibration reaction are not particularly limited, but typically, the reaction is carried out by heating and stirring the mixture described above at a temperature of 30 to 250° C. From the perspective of effectively carrying out the reaction, the reaction temperature is preferably in a range from 80° C. to 200° C., and particularly preferably in a range from 100° C. to 150° C. In the method for producing the liquid aryl group-containing polyorganosiloxane according to the present invention, after heating and stirring at a temperature in the range from 80° C. to 200° C., generated water is removed from the system as necessary and, furthermore, the resulting mixture is heated to reflux. Particularly, in cases where using an organic solvent, equilibration reaction can be easily performed at the reflux temperature by selecting an organic solvent having a boiling point in a range from 80 to 200° C. On the other hand, it is not preferable that the temperature is below the lower limit described above because the equilibration reaction will not be sufficiently carried out or will take an extended period of time, leading to a decline in industrial production efficiency. Likewise, it is not preferable that the temperature is excessively high because the organic groups bonded to the silicon atoms may decompose.

In cases where phenyltrimethoxysilane, naphthyltrimethoxysilane, or a similar hydrolysable organosilane is used as the component (A-1), the desired liquid aryl group-containing polyorganosiloxane can be obtained by adding a necessary amount with respect to the hydrolysable groups or an excessive amount of water to the reaction system, and carrying out the equilibration reaction described above while carrying out a hydrolysis reaction. If the hydrolysis reaction is not sufficiently completed and hydrolysable group remain, in cases when mixed with an oil agent, the resulting liquid aryl group-containing polyorganosiloxane have problems such as being prone to hydrolysis, which leads to becoming turbid over time and lacking stability as a cosmetic raw material or cosmetic product.

The equilibration reaction can be stopped by cooling the system at a desired time. The alkali metal catalyst used in the reaction is neutralized using carbonic acid gas, acetic acid, hydrochloric acid, or a similar acidic substance or trimethylchlorosilane or a similar chlorosilane so as to form a neutral salt and, as a result, can be easily removed from the system through filtration, rinsing, or the like. Note that the progression of the equilibration reaction is measured by sampling a small amount of the reaction liquid and neutralizing this sample and, thereafter, measuring the molecular weight or the viscosity of the resulting liquid aryl group-containing polyorganosiloxane (neutralized sample). Thus, a liquid aryl group-containing polyorganosiloxane having a desired viscosity or molecular weight can be obtained.

The unreacted component (A-2) is redundant with an oil agent (B) (hereinafter described) as a component and, therefore, a composition comprising the obtained liquid aryl group-containing polyorganosiloxane according to the present invention and the unreacted component (A-2) constitutes the aryl group-containing polyorganosiloxane composition according to the present invention and, as desired, can be used as-is as a cosmetic raw material.

In some cases, the solvent may cause a reduction in the refractive index of the composition thus, after re-equilibrating, is preferably removed via a known technique such as stripping or the like. The degree to which pressure is reduced and the method of distilling off the solvent can be appropriately selected depending on the capacity of the apparatus and the scale of the reaction, but the content of the organic solvent in the obtained liquid aryl group-containing polyorganosiloxane is preferably less than 3 wt. % and more preferably is from 0 to 2 wt. %. The content of the organic solvent is most preferably substantially 0 wt. %.

Next, an aryl group-containing polyorganosiloxane composition comprising: (A) the liquid aryl group-containing polyorganosiloxane according to the present invention and (B) an oil agent will be described. The liquid aryl group-containing polyorganosiloxane (A) according to the present invention is a component that is usable alone as a high refractive index oil agent, but when mixed with an oil agent, is further improved in terms of usability as a cosmetic raw material.

Specifically, the aryl group-containing polyorganosiloxane composition of the present invention imparts a high overall refractive index to the composition and the liquid aryl group-containing polyorganosiloxane is uniformly miscible with the other oil agents. Thus, there are benefits in that compounding stability in a cosmetic composition and handling are superior, the viscosity thereof is easily adjustable, and turbidity that accompanies hydrolysis does not occur, even when stored over an extended period of time. Moreover, makeup finish with depth can be attained using a small amount, and a youthful, bright texture can be provided to the lips, around the eyes, and the like. Furthermore, there are benefits in that makeup running does not easily occur and cosmetic effects are maintained over an extended period of time.

The overall refractive index of the composition of the present invention is not less than 1.45, and an overall viscosity at 25° C. of the composition is in a range of 100 to 100,000 mPa·s. The liquid aryl group-containing polyorganosiloxane (A) according to the present invention has superior miscibility and compatibility with the optional oil agent (B) and, as a result, the overall viscosity of the composition can be adjusted and improvements in the shine, feeling of sheerness, and sensation during use of the cosmetic composition can be achieved while maintaining a high refractive index. The overall refractive index of the composition is preferably in a range from 1.45 to 1.60. While not limited thereto, particularly, it is preferable that an oil agent (B) having a refractive index of not less than 1.45 is used. However, there is a benefit in that even in cases where the composition comprises an oil agent with a low refractive index of less than 1.45, a composition having a high refractive index can be easily prepared by adjusting the compounding ratio of the component (A) (which has excellent compatibility with the oil agent (B)).

The compounding ratio of the liquid aryl group-containing polyorganosiloxane (A) according to the present invention and the optional oil agent (B) can be set as desired but, specifically, by adjusting the compounding ratio of the component (A) to the component (B) to be in a range from 1:0.1 to 1:10, a phenyl group-containing organopolysiloxane composition having an overall refractive index of the composition in the range from 1.45 to 1.60 and an overall viscosity of the composition in the range from 100 to 100,000 mPa·s at 25° C. can be easily obtained. Particularly, when using a disiloxane or a trisiloxane having a viscosity at 25° C. of not more than 250 mPa·s as the component (B), there are benefits in that a desired composition having a high refractive index, and low to high viscosity can be obtained extremely easily by adjusting the compounding ratio of the component (A) to the component (B) to be in the range from 1:0.1 to 1:10.

The liquid aryl group-containing polyorganosiloxane (A) according to the present invention has superior compatibility with oil agents and the viscosity at 25° C. thereof can be set to be relatively low. As a result, the overall viscosity of the composition can easily be adjusted to be in the range from 100 to 100,000 mPa·s. The overall viscosity of the composition is more preferably in a range from 500 to 50,000 mPa·s. If the viscosity of the composition exceeds the upper limit described above, handling as a cosmetic raw material may decline. If the viscosity is below the lower limit described above, in cases where the liquid aryl group-containing polyorganosiloxane (A) according to the present invention is used, preparation will be difficult unless an oil agent with extremely low viscosity is used and characteristics as a high refractive index raw material may not be fully performed.

Examples of the oil agent (B) include one type or two or more types of oil agents selected from silicone oils, hydrocarbon oils, ester oils, vegetable oils and fats, animal oils and fats, higher alcohols, liquid fatty acids, triglycerides, and artificial sebums. Particularly, an oil agent having a refractive index of not less than 1.45 is preferable, but the oil agent is not limited thereto and even in cases where the oil agent is a higher fatty acid ester, benzoic acid ester, or similar non-silicone oil agent, a high refractive index aryl group-containing polyorganosiloxane composition can be obtained by blending the oil agent at a desired ratio. Note that these oil agents are specifically described in Patent Document 6 (Japanese Unexamined Patent Application Publication No. 2011-136935), but are not limited thereto.

Particularly, from the perspectives of compatibility with the component (A) and overall sensation during use of the composition, the component (B) is preferably a phenyl group-containing organopolysiloxane. Examples thereof include a methylphenylpolysiloxane capped at both molecular terminals with trimethylsiloxy groups, a dimethylsiloxane.methylphenylsiloxane copolymer capped at both molecular terminals with trimethylsiloxy groups, a diphenylpolysiloxane capped at both molecular terminals with trimethylsiloxy groups, a dimethylsiloxane.diphenylsiloxane copolymer capped at both molecular terminals with trimethylsiloxy groups, and a trimethylpentaphenyltrisiloxane.

The component (B) of the present invention is particularly preferably a phenyl group-containing organopolysiloxane represented by structural formula (2-1) or structural formula (2-2) below. In these formulae, $R^2$ is synonymous with that described above and, in terms of molar ratio, at least 50% of the $R^2$ moieties are phenyl groups, n1 or n2 is a number in a range of 0 to 1,000; and n3 is a number in a range of 1 to 1,000. n1 or n2 is preferably a number in a range from 0 to 10, and n3 is preferably a number in a range from 1 to 10. Particularly, n1 is preferably a number in a range from 0 to 5, n3 is a number in a range from 1 to 5, and (n2+n3) is a number in a range from 2 to 5.

Structural formula (2):

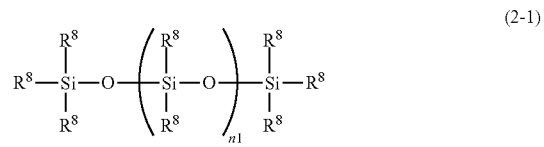

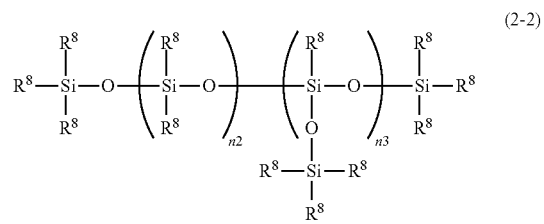

The viscosity at 25° C. of the phenyl trimethicone, phenyl tetrasiloxane, phenyl trisiloxane, or phenyl disiloxane represented by the structural formulae (2-1) or (2-2) is not more than 250 mPa·s, and the refractive index is not less than 1.55 and, therefore this compound is most suitable as the component (B) of the present invention. Taking advantage of these characteristics, there is a benefit in that a cosmetic raw material can be provided which, when combined with an inorganic powder, suppresses white flaking of the inorganic powder, is free of stickiness, enhances transparency, and imparts a natural luster to the skin or hair that is free of unnatural glare.

Of the oil agents, at least one type of oil agent selected from polybutene, polybutene hydride, paraffin wax, petrolatum, lanolin, beeswax, carnauba wax, candelilla wax, stearyl alcohol, lauric acid, myristic acid, palmitic acid, stearic acid, isostearic acid, behenic acid, lanolin fatty acid, hydrogenated castor oil, and the like is preferably compounded in the composition of the present invention as a base material of a makeup cosmetic composition, particularly a base material of a makeup cosmetic composition for application to the lips, around the eyes, or to the eyelashes.

A process for uniformly mixing these components and obtaining the aryl group-containing polyorganosiloxane composition of the present invention is not particularly limited, and examples thereof include a method of kneading at room temperature using a ball mill, an oscillating mill, a kneader/mixer, a screw extruder, a paddle mixer, a ribbon mixer, a Banbury mixer, a Ross mixer, a Henschel mixer, a flow jet mixer, a Hobart mixer, a roll mill, or similar conventionally known mixing device or kneading apparatus.

Furthermore, the liquid aryl group-containing polyorganosiloxane (A) according to the present invention can be arbitrarily blended and uniformly dissolved in an organic UV absorber or one or more types of oleophilic cosmetic raw material (C), along with the oil agent (B). Therefore, compared to a conventional phenyl group-containing organopolysiloxane, compositional degree of freedom and compounding stability are superior.

The one or more types of oleophilic cosmetic raw material (C) is a lipophilic raw material for use in cosmetic products, and is not particularly limited provided that it is a material other than the oil agents described above. Examples thereof include oil agent thickeners and gelling agents, and organic ultraviolet light blocking components. Particularly, the liquid aryl group-containing polyorganosiloxane (A) according to the present invention has extremely high compatibility with organic ultraviolet light blocking components and can be uniformly dissolved in a small amount of most organic ultraviolet light blocking components such as salicylic acid-based, PABA-based, benzophenone-based, cinnamic acid-based, and benzoylmethane-based organic ultraviolet light blocking components, and the like. Moreover, the component (A) has high compatibility with ethylhexyl methoxycinnamate and similar UV-B ultraviolet light blocking components and diethylamino hydroxybenzoyl benzoic acid and similar UV-A ultraviolet light blocking components. Therefore, the component (A) is useful in that even in cases where a plurality of ultraviolet light blocking components are combined and compounded, compounding stability does not decline.

Note that these oil agent thickeners and gelling agents, and organic ultraviolet light blocking components are specifically described in Patent Document 6 (Japanese Unexamined Patent Application Publication No. 2011-136935), but are not limited thereto.

The compounding ratio of the liquid aryl group-containing polyorganosiloxane (A) according to the present invention to the optional one or more types of oleophilic cosmetic raw material (C) can be set as desired. However, by specifically adjusting the compounding ratio of the component (A) to the component (C) to be in a range from 1:0.1 to 1:10, a uniform mixture can be obtained even when using an oleophilic cosmetic raw material having low solubility with respect to known phenyl group-containing organopolysiloxanes such as an organic ultraviolet light blocking component.

Furthermore, a composition comprising the liquid aryl group-containing polyorganosiloxane (A) according to the present invention may comprise a powder or coloring agent (D) in addition to the component (B) and/or the component (C). The powder or coloring agent can be uniformly mixed with the components (A) to (C) and, specifically combining a powder component, particularly an inorganic powder or pearl pigment, the powder or coloring agent can be used as a cosmetic raw material that increases the feeling of sheerness and that imparts a natural luster and brilliance to the skin or hair that is free of unnatural glare. Particularly, the liquid aryl group-containing polyorganosiloxane of the present invention has superior affinity with the powder or coloring agent (pigment or the like) and, specifically, pre-compounding the liquid aryl group-containing polyorganosiloxane with a coloring agent is beneficial in that color variations of the entire product can be suppressed and color adjustment of various cosmetic compositions can be easily and simply performed.

Additionally, the novel liquid aryl group-containing polyorganosiloxane according to the present invention has a higher refractive index than conventionally known silicone-based oil agents and, therefore, when used in combination with titanium oxide or a similar high refractive index powder component, a difference between the refractive indices of the powder and the oil agent will be small. As a result, there are advantages in that the feeling of sheerness on the skin is superior and white flaking on the skin will not occur and, thus, a natural appearance can be obtained. Typically, in powder foundations and similar make-up cosmetic compositions containing a high amount of titanium oxide (refractive index: approx. 2.70) or a similar high refractive index cosmetic composition use powder, dimethicone or a similar silicone-based oil agent is used for the purpose of preventing agglomeration of the cosmetic composition. Here, in cases where the difference between the refractive indices of the powder and the silicone-based oil agent is large, there will be demerits such as overall, the product will appear white and the feeling of sheerness on the skin and natural finish will be negatively affected. However, with the novel liquid aryl group-containing polyorganosiloxane according to the present invention, there are benefits in that a silicone-based oil agent having a refractive index from 1.55 to 1.60 can easily be provided, the difference in refractive indices can be suppressed, and a make-up cosmetic composition, a skin cosmetic composition for skin care use, and the like having a superior feeling of sheerness can be provided.

On the other hand, silicone elastomer particles having a relatively low refractive index (refractive index: approx. 1.40 to 1.50) are frequently compounded in foundations, make up bases, and similar cosmetic compositions for the purpose of concealing wrinkles (soft focus effect). However, when a dimethyl silicone oil or similar conventional oil agent for use in cosmetic products is used, the refractive indices of the oil agent and the particles are similar and, as a result, transparency after application may be high and the soft focus effects may be insufficient. In contrast, with the novel liquid aryl group-containing polyorganosiloxane according to the present invention, a silicone-based oil agent having a refractive index from 1.55 to 1.60 can easily be provided. Therefore, there are benefits in that the difference between the refractive indices of the novel liquid aryl group-containing polyorganosiloxane and the silicone elastomer will be great and, as a result, the product will not be transparent on the skin and the soft focus effects of the silicone elastomer particles are further improved.

Additionally, the component (D) is a powder and/or a coloring agent for use in a cosmetic composition, and this powder and/or coloring agent can be any powder provided that it is normally used in cosmetic compositions, and is not limited to form (sphere, bar, needle, plate, amorphous, spindle, or the like), particle size (aerosol, micro-particle, pigment-grade particle, or the like), or particle structure (porous, nonporous, or the like) thereof. When compounding the powder and/or coloring agent as a pigment, preferably one or two or more selected from an inorganic pigment powder, an organic pigment powder, and a resin powder having an average diameter in a range from 1 nm to 20 μm is compounded. Note that the powder or coloring agent is specifically described in Patent Document 6 (Japanese Unexamined Patent Application Publication No. 2011-136935), but is not limited thereto. Furthermore, as described in said patent Document 6 (JP2011-136935A), it is recommended to subject the aforementioned powders or colorants to a water-repellant treatment. Additionally, it is possible to combine the powders with colorants and/or to combine different colorants, or to add conventional oil agents, silicones other than the organopolysiloxanes of the invention, as well as fluoro-compounds, to subject the powders or coloring agents to surface treatment with surface-active substances, and, if necessary, to combine the powders and colorants of two or more different types. Examples of the aforementioned water-repellant treatment of the powders and/or coloring agents are specifically described in said Patent Document 6, but are not limited thereto. Especially, the component (D) may be subject to the treatment with perfluoroalkylsilane, perfluoroalkylphosphate, perfluoropolyester, or with another perfluoro-compound.

The liquid aryl group-containing polyorganosiloxane (A) of the present invention and the composition comprising the same provide a high refractive index without turbidity that accompanies hydrolysis occurring when stored for an extended period of time and are uniformly miscible with various cosmetic raw materials and, thus, in light of superior compounding stability in cosmetic compositions and handling, can be suitably used as cosmetic raw materials. In cases where the cosmetic raw material is compounded in a cosmetic composition, the durability, moisture resistance, affinity to the skin, water repellency, softness, water vapor transmittance, gas transmittance, film forming, filler retention, and lubricity of the cosmetic composition are improved and, furthermore, sensation during use can be greatly improved in that stickiness is not produced. Particularly, the cosmetic raw material can enhance the transparency of the cosmetic composition and can impart lasting presence, shine, brilliance, and luster to the cosmetic composition when used. Moreover, when combined with an inorganic powder or a pearl pigment, white flaking of the cosmetic composition can be suppressed and a natural shine (gloss) that is free of unnatural glare can be imparted to the skin or hair.

The liquid aryl group-containing polyorganosiloxane (A) and the composition comprising the same according to the present invention enhance the feeling of sheerness of a cosmetic composition comprising said composition, can impart presence, shine, and luster when applied to the skin or lips, suppress makeup running, and have superior durability of cosmetic effects. Therefore, the liquid aryl group-containing polyorganosiloxane (A) and the composition comprising the same according to the present invention are particularly useful as cosmetic raw materials used in glossy makeup cosmetic compositions where brilliance and a feeling of sheerness is required. Furthermore, the liquid aryl group-containing polyorganosiloxane of the present invention, in cases where compounded in a cosmetic composition, is superior in terms of sensation during use, particularly luster, skin compatibility, and the like, and is advantageous in that pore concealing (soft focus) and a natural finish can be achieved. Moreover, in hair cosmetic composition combined with the liquid aryl group-containing organopolysiloxane, the hair cosmetic composition imparts excellent frizz control benefit to human hair. Thus, the liquid aryl group-containing polyorganosiloxane of the present invention is also extremely useful as a cosmetic raw material in skin cosmetic compositions such as skin care cosmetic compositions and the like and hair cosmetic compositions such as hair conditioners and the like.

A compounded amount of the liquid aryl group-containing polyorganosiloxane (A) according to the present invention in a cosmetic composition can be appropriately selected based on the type, form, and desired characteristics of the cosmetic composition, along with the balance with other components but typically, in the case of makeup cosmetic compositions, skin cosmetic compositions, or hair cosmetic compositions, is preferably within a range of 0.5 to 50 wt. % and particularly within a range of 1.0 to 20 wt. % of the overall cosmetic composition.

The cosmetic composition of the present invention can comprise at least one type of compound selected from an oil agent (B) (specifically a wax and a volatile oil agent), an organic UV light blocker or similar oleophilic cosmetic raw material (C), a powder or coloring agent (D), a surfactant (E), a film-forming agent (F), a water-soluble polymer (G), a UV light blocker (H), a lower monohydric alcohol (I), a polyhydric alcohol (J), and water (K) in addition to the liquid aryl group-containing polyorganosiloxane (A). Moreover, it is particularly preferable that the cosmetic composition of the present invention is a makeup cosmetic composition comprising these components. Additionally, preferable amounts of these cosmetic composition components can be appropriately determined based on known cosmetic composition formulations (compositions).

At least one compound selected from the group consisting of an amino acid or salt, an inorganic salt, an organic acid or a salt thereof can be compounded in the cosmetic composition of the present invention, as appropriate according to the function of the cosmetic composition.

Furthermore, components that are typically compounded in cosmetic compositions such as plant extracts and similar bioactive substances, pH adjusting agents, antioxidants, chelating agents, moisturizing components, perfumes, preservatives, and the like can be compounded in the cosmetic composition of the present invention, but these components are not limited thereto. Additionally, these components are used to an extent in which the effects of the present invention are not impaired.

Note that these components are specifically described in Patent Document 6 (Japanese Unexamined Patent Application Publication No. 2011-136935), but are not limited thereto.

Particularly, a cosmetic composition comprising the liquid aryl group-containing polyorganosiloxane (A) of the present invention is preferably a makeup cosmetic composition, a hair cosmetic composition, or a skin cosmetic composition. Of these, a makeup cosmetic composition is preferable and such a cosmetic composition can be suitably used as a makeup cosmetic composition to be applied to the lips/around the eyes/eyelashes of the parts of the face. In cases where the makeup cosmetic composition according to the present invention is applied to these locations, there are benefits in that elution and makeup running caused by perspiration or sebum can be continuously suppressed and a finish with presence on the skin can be achieved. Moreover, texture having a feeling of sheerness, shine, brilliance, and luster can be imparted, pore concealing (soft focus) effects can be enhanced, and coloration can be easily adjusted. This preferable cosmetic composition may be lip cream, paste rouge, lip gloss, rouge, lip liner, or similar lip cosmetic composition; or eye shadow, mascara, eye liner, eyebrow liner, eye color, or similar eye makeup cosmetic composition. Note that specific examples, forms, production methods, and packages are specifically described in Patent Document 6 (Japanese Unexamined Patent Application Publication No. 2011-136935), but are not limited thereto. Likewise, a cosmetic composition comprising the liquid aryl group-containing polyorganosiloxane (A) of the present invention is preferable as a skin care cosmetic composition, and is useful in that sensation during use (i.e. skin compatibility) is superior, and that a natural finish can be achieved.

The liquid aryl group-containing polyorganosiloxane (A) according to the present invention can be used in the same applications recited for the cosmetic raw material and the glossy cosmetic composition described in Japanese Unexamined Patent Application Publication No. 2011-136935 proposed by the present applicant. Likewise, a composition comprising the novel liquid aryl group-containing organopolysiloxane according to the present invention and an oil agent can be used in the same applications recited for the phenyl silsesquioxane resin compositions described in Japanese Unexamined Patent Application Publication (Translation of PCT Application) No. 2007-535586 and Japanese Unexamined Patent Application Publication No. 2009-019033. More specifically, the liquid aryl group-containing polyorganosiloxane (A) according to the present invention can be used partially or completely in place of the phenyl group-containing organopolysiloxane compositions or the various phenyl silsesquioxane resin compositions described in these Patent Documents and such usage forms are encompassed within the scope of the present invention.

While not limited thereto, examples of specific products include the makeup cosmetic compositions and the skin care cosmetic compositions described above, skin cleansing products, anti-perspirant products, ultraviolet light blocking products, and similar skin use cosmetic products; hair cleansing products, hair dressing products, hair coloration products, hair growing products, hair rinse products, hair conditioner products, hair treatment products, and similar scalp use cosmetic products; bath use cosmetic products; hair regrowth agents, hair growth promoters, analgesics, germicides, anti-inflammatory agents, refreshing agents, and skin anti-aging agents.

The skin use cosmetic products can be used on any site of the entire body including the scalp, face (including lips, eyebrows, and cheeks), fingers, and fingernails. Specific examples thereof include cleansing gels, cleansing creams, cleansing foams, face washing creams, eye makeup removers, face washing foams, liquid soaps (body soaps), hand soaps, gel-like soaps, shaving creams, nail polish removers, acne treatment cosmetic compositions, and similar skin cleansing agent products; skin creams, scalp treatments, skin milks, milk lotions, emulsions, facial packs, body powders, essences, shaving lotions, massage lotions, and similar skin care products; foundations, liquid foundations, oil-based foundations, makeup bases, powders, face powders, cheek coloring, lip creams, lipsticks, lip glosses, eye creams, mascaras, eyebrow pencils, eyelash cosmetic products, and similar makeup products; deodorants and similar anti-perspirants; and sunscreen agents, tanning use medicaments (sun tanning agent), and similar ultraviolet light blocking products.

Examples of scalp use cosmetic products include shampoos, rinse-in shampoos, and similar hair use cleansing agents; hair waxes, hair use curl holding agents, setting agents, hair creams, hairsprays, hair liquids, and similar hair dressing products; hair coloring substances, hair color sprays, hair color rinses, hair color sticks, and similar hair use coloration products; hair tonics, hair treatment essences, hair packs, and similar hair growing products; and oil rinses, cream rinses, treatment rinses, hair conditioners, hair treatments, and similar hair rinse or hair conditioning products. In addition, examples of bath use cosmetic products include bath foams.

The form of the cosmetic composition according to the present invention is not particularly limited, and these can be preferably used in the form of a liquid, W/O emulsion, O/W emulsion, W/O cream-like, O/W cream-like, solid, paste-like, gel-like, powder-like, multi-layer, mousse-like, mist-like, granule, flake, crushed stone, and similar forms. Particularly preferable forms are W/O creams, solids, pastes, gels, and powders.

EXAMPLES

Hereinafter, the present invention is described in detail with reference to Practical Examples and Comparative Examples, but it should be understood that the present invention is not limited to these Practical Examples. Particularly, the formulation of the cosmetic composition according to the present invention should not be construed to be limited to the formulations disclosed in the following Practical Examples. The value of viscosity (kinetic viscosity) is measured at 25° C. In the Practical Examples and the Comparative Examples, "Ph" is a phenyl group, "Me" is a methyl group, and "Np" is a 1-naphthyl group. "$T^{Ph}$ unit" is a phenylsiloxy unit represented by $PhSiO_{3/2}$ and "phenylsilsesquioxane constituted solely by $T^{Ph}$ units" is a solid phenylsilsesquioxane constituted by these units. Note that, prior to the descriptions of the Practical Examples and the Comparative Examples, methods for measuring the physical properties of the components and methods of evaluating the samples are described.

Viscosity of the organopolysiloxane or the organopolysiloxane composition Viscosity was measured at 25° C. using a single cylinder rotational viscometer (Vismetron VG-A1, manufactured by Shibaura Systems, Co., Ltd.).

Measurement of weight average molecular weight and average degree of polymerization In the Practical Examples and the Comparative Examples, the weight average molecular weight (Mn) was determined from the calibration curve from the measurement results of gel permeation chromatography (GPC) conducted under the following conditions and is expressed in terms of polystyrene standard.
Measurement temperature: 40° C. (column oven temperature)
Sample: Organopolysiloxane used as a 1 wt. % toluene solution
Detector: RI detector
Calibration curve polymer: Standard polystyrene
Measurement of the Refractive Index (RI)
The refractive index of the components and the organopolysiloxane composition were measured using an Abbe refractometer.
Appearance Evaluation of the Organopolysiloxane Composition
Each of the organopolysiloxanes or compositions were placed in a glass container and visually evaluated by the following standards.
Transparent: Sample is clear with no turbidity
Turbid: Sample is white, cloudy, and not transparent
NMR Structural Analysis
The structure of each of the organopolysiloxanes was determined by using $^{29}$Si-nuclear magnetic resonance spectroscopic analysis (JNM-ECA500, manufactured by JEOL Ltd.).

Practical Example 1

40 g of a phenylsilsesquioxane constituted solely by $T^{Ph}$ units (217 FLAKE RESIN, manufactured by Dow Corning Toray Co., Ltd.) and 60 g of toluene were introduced to a 500 mL flask provided with a thermometer, a Dean-Stark trap, and a refluxing cooler. The system was mixed until uniform. Then, 200 g of trimethylpentaphenyltrisiloxane, 40 g of tetraphenyldimethyldisiloxane, and 0.13 g of cesium hydroxide were added thereto, and the generated water was distilled off while heating. Then, the system was heated to reflux for 4 hours. The system was cooled, and then 1 g of acetic acid was added thereto in order to neutralize the system. Then, the generated salt was filtered off and the filtrate was heated under reduced pressure in order to distill off the toluene. Thus, 237 g of a colorless, transparent, viscous liquid was obtained. Regarding this liquid, it was confirmed that viscosity was 1070 mPa·s, weight average molecular weight was 770, and refractive index was 1.578. Moreover, it was confirmed via $^{29}$Si-nuclear magnetic resonance spectroscopic analysis that the liquid was a phenyl group-containing siloxane compound represented by the structural formula:

$(Ph_2MeSiO_{1/2})_{0.51}(PhMeSiO_{2/2})_{0.28}(PhSiO_{3/2})_{0.21}$

The number of moles of phenyl groups per 1 mole of Si atoms in the molecule was 1.51.

Practical Example 2

Other than using 50 g of the phenylsilsesquioxane constituted solely of $T^{Ph}$ units (as above), 142.5 g of trimethylpentaphenyltrisiloxane, and 47.5 g of tetraphenyldimethyldisiloxane, Practical Example 2 was synthesized via the same procedure as that of Practical Example 1. Thus, 236 g of a colorless, transparent, viscous liquid was obtained. Regarding this liquid, it was confirmed that viscosity was 1760 mPa·s, weight average molecular weight was 810, and refractive index was 1.579. Moreover, it was confirmed via $^{29}$Si-nuclear magnetic resonance spectroscopic analysis that the liquid was a phenyl group-containing siloxane compound represented by the structural formula:

$$(Ph_2MeSiO_{1/2})_{0.49}(PhMeSiO_{2/2})_{0.26}(PhSiO_{3/2})_{0.25}$$

The number of moles of phenyl groups per 1 mole of Si atoms in the molecule was 1.49.

Practical Example 3

Other than using 60 g of the phenylsilsesquioxane constituted solely of $T^{Ph}$ units (as above), 135 g of trimethylpentaphenyltrisiloxane, and 45 g of tetraphenyldimethyldisiloxane, Practical Example 3 was synthesized via the same procedure as that of Practical Example 1. Thus, 236 g of a colorless, transparent, viscous liquid was obtained. Regarding this liquid, it was confirmed that viscosity was 2950 mPa·s, weight average molecular weight was 850, and refractive index was 1.579. Moreover, it was confirmed via $^{29}$Si-nuclear magnetic resonance spectroscopic analysis that the liquid was a phenyl group-containing siloxane compound represented by the structural formula:

$$(Ph_2MeSiO_{1/2})_{0.44}(PhMeSiO_{2/2})_{0.26}(PhSiO_{3/2})_{0.30}$$

The number of moles of phenyl groups per 1 mole of Si atoms in the molecule was 1.44.

Practical Example 4

Other than using 70 g of the phenylsilsesquioxane constituted solely of $T^{Ph}$ units (as above), 127.5 g of trimethylpentaphenyltrisiloxane, and 42.5 g of tetraphenyldimethyldisiloxane, Practical Example 4 was synthesized via the same procedure as that of Practical Example 1. Thus, 235 g of a colorless, transparent, viscous liquid was obtained. Regarding this liquid, it was confirmed that viscosity was 5530 mPa·s, weight average molecular weight was 900, and refractive index was 1.579. Moreover, it was confirmed via $^{29}$Si-nuclear magnetic resonance spectroscopic analysis that the liquid was a phenyl group-containing siloxane compound represented by the structural formula:

$$(Ph_2MeSiO_{1/2})_{0.42}(PhMeSiO_{2/2})_{0.23}(PhSiO_{3/2})_{0.35}$$

The number of moles of phenyl groups per 1 mole of Si atoms in the molecule was 1.42.

Practical Example 5

Other than using 80 g of phenylsilsesquioxane constituted solely of $T^{Ph}$ units, 120 g of trimethylpentaphenyltrisiloxane, and 40 g of tetraphenyldimethyldisiloxane, Practical Example 5 was synthesized via the same procedure as that of Practical Example 1. Thus, 234 g of a colorless, transparent, viscous liquid was obtained. Regarding this liquid, it was confirmed that viscosity was 11460 mPa·s, weight average molecular weight was 940, and refractive index was 1.579. Moreover, it was confirmed via $^{29}$Si-nuclear magnetic resonance spectroscopic analysis that the liquid was a phenyl group-containing siloxane compound represented by the structural formula:

$$(Ph_2MeSiO_{1/2})_{0.38}(PhMeSiO_{2/2})_{0.22}(PhSiO_{3/2})_{0.40}$$

The number of moles of phenyl groups per 1 mole of Si atoms in the molecule was 1.38.

Practical Example 6

30 g of 1-naphthyltrimethoxysilane (Z-6874, manufactured by Dow Corning Toray Co., Ltd.), 90 g of trimethylpentaphenyltrisiloxane, and 120 g of toluene were introduced to a 300 mL flask provided with a thermometer, a Dean-Stark trap, and a refluxing cooler. The system was mixed until uniform. Then, a mixed liquid comprising 0.06 g of cesium hydroxide, 5 g of ion exchanged water, and 5 g of methanol was added dropwise to the system. Methanol generated as a result of the hydrolysis reaction was removed while heating and, furthermore, excess water was removed via azeotropic dehydration with toluene. After the dehydration, the system was heated to reflux for 4 hours. The system was cooled, and then 0.5 g of acetic acid was added thereto in order to neutralize the system. Then, the generated salt was filtered off and the filtrate was heated under reduced pressure in order to distill off the toluene. Thus, 109 g of a colorless, transparent, viscous liquid was obtained. Regarding this liquid, it was confirmed that viscosity was 12100 mPa·s, weight average molecular weight was 730, and refractive index was 1.596. Moreover, it was confirmed via $^{29}$Si-nuclear magnetic resonance spectroscopic analysis that the liquid was a phenyl group/1-naphthyl group-containing siloxane compound represented by the structural formula:

$$(Ph_2MeSiO_{1/2})_{0.53}(PhMeSiO_{2/2})_{0.27}(NpSiO_{3/2})_{0.20}$$

The total number of moles of naphthyl groups and phenyl groups per 1 mole of Si atoms in the molecule was 1.53.

Compounded amounts, physical properties, and structures (ratio of each structural unit) for the samples (Nos. 1 to 6) of Practical Examples 1 to 6 are compiled and shown in Table 1 (Formulation and Physical Properties of the Liquid Aryl Group-containing Polyorganosiloxane) below.

Table 1: Formulation and Physical Properties of the Liquid Aryl Group-Containing Polyorganosiloxane

TABLE 1

|  |  | Practical Examples | | | | | |
| --- | --- | --- | --- | --- | --- | --- | --- |
|  |  | 1 | 2 | 3 | 4 | 5 | 6 |
| <Sample No.> | | No. 1 | No. 2 | No. 3 | No. 4 | No. 5 | No. 6 |
| Raw material (g) | (A-1) Phenylsilsesquioxane | 40 | 50 | 60 | 70 | 80 | |
| | (A-1') 1-Naphthyltrimethoxysilane | | | | | | 30 |
| | (A-2-1) Trimethylpentaphenyltrisiloxane | 200 | 142.5 | 135 | 127.5 | 120 | 90 |
| | (A-2-2) Tetraphenyldimethyldisiloxane | 40 | 47.5 | 45 | 42.5 | 40 | |

TABLE 1-continued

|  | Practical Examples | | | | | |
| --- | --- | --- | --- | --- | --- | --- |
|  | 1 | 2 | 3 | 4 | 5 | 6 |
| <Physical properties of the samples> | | | | | | |
| Viscosity | 1070 | 1760 | 2950 | 5530 | 11460 | 12100 |
| Refractive index | 1.578 | 1.579 | 1.579 | 1.579 | 1.579 | 1.596 |
| Appearance immediately after manufacturing | Transparent | Transparent | Transparent | Transparent | Transparent | Transparent |
| Appearance after 4 months at 50° C. | Transparent | Transparent | Transparent | Transparent | Transparent | Transparent |
| Weight average molecular weight | 770 | 810 | 850 | 900 | 940 | 730 |
| ($Ph_2MeSiO_{1/2}$) units | 0.51 | 0.49 | 0.44 | 0.42 | 0.38 | 0.53 |
| ($PhMeSiO_{2/2}$) units | 0.28 | 0.26 | 0.26 | 0.23 | 0.22 | 0.27 |
| ($PhSiO_{3/2}$) units | 0.21 | 0.25 | 0.30 | 0.35 | 0.40 | |
| ($NpSiO_{3/2}$) units | | | | | | 0.20 |
| Total number of moles of aryl groups per 1 mole of Si atoms | 1.51 | 1.49 | 1.44 | 1.42 | 1.38 | 1.53 |

Evaluation Using Collagen Film

Using collagen film having a structure similar to skin, the thickness and durability on skin of the liquid aryl group-containing polyorganosiloxane according to the present invention (sample No. 4) were evaluated according to the following methods.

1. 0.1 g of sample No. 4 and trimethylpentaphenyltrisiloxane, respectively, were applied dropwise on a collagen film (Collagen Food Film, manufactured by Naturin GmbH) and the appearance of the sample immediately thereafter was observed (FIG. 1).
2. Next, changes in the appearance of the sample (FIG. 2) were observed after gently pressing down on the sample with a two-ply (single piece) of tissue paper (Joy Botanica 170, manufactured by Oji Nepia Co., Ltd.).

Figure 2:
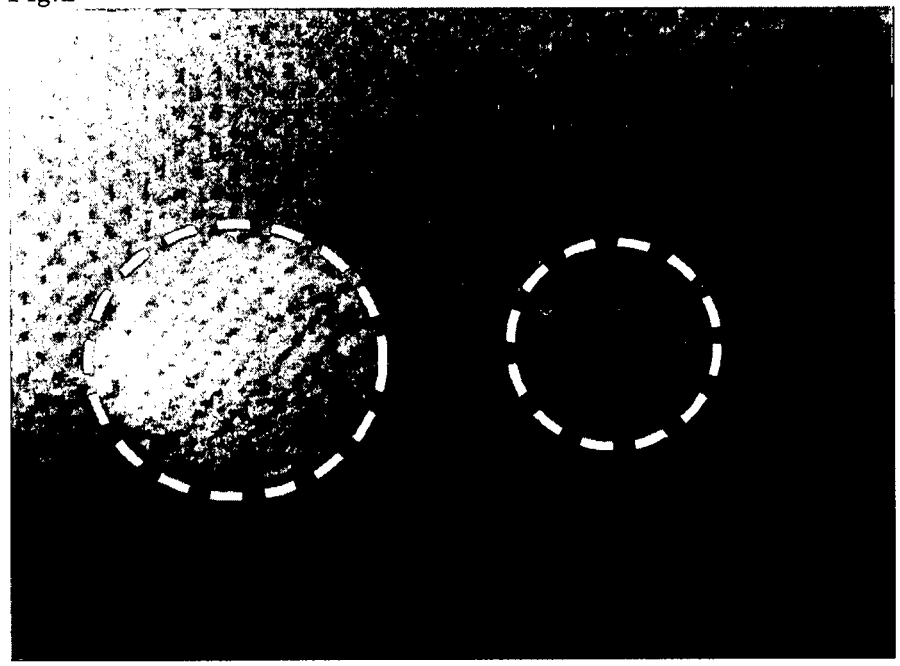
FIG. 2 depicts the appearance of the samples of FIG. 1 after lightly applying a sheet of tissue paper on the samples (the white dotted lines indicate the approximate periphery of the range of spreading of the samples).

Results of the evaluations described above are shown in FIG. 1 and FIG. 2. The right sample is the liquid aryl group-containing polyorganosiloxane according to the Practical Example (sample No. 2) and the left sample is methylpentaphenyltrisiloxane. In FIG. 2, the white dotted lines indicate the approximate periphery of the range of spreading of the samples.

A portion of the liquid aryl group-containing polyorganosiloxane (sample No. 2) migrated to the tissue paper after the tissue paper was applied, but the oil agent layer had thickness, did not spread greatly, and maintained a shiny appearance (FIG. 2, right).

On the other hand, with the methylpentaphenyltrisiloxane, the oil agent soaked into the tissue paper or the collagen film after the tissue paper was applied and spread out widely. Moreover, thickness and shine were not observed (FIG. 2, left).

Practical Examples 7 and 8

Organopolysiloxane compositions of the present invention (sample Nos. 7 and 8) were prepared according to the formulations shown in Table 2 by mixing the liquid aryl group-containing polyorganosiloxane of the present invention (sample No. 2 or No. 3) and trimethylpentaphenyltrisiloxane at a weight ratio of 20:80 until uniform, using mechanical force (a mixer) at a temperature of 120° C. Evaluation results of the viscosity, refractive index, appearance immediately after preparation, and appearance after storage are shown for each sample in the Table.

Moreover, evaluation results of the individual viscosity, refractive index, appearance immediately after preparation, and appearance after storage of the liquid aryl group-containing polyorganosiloxane of the present invention (sample No. 2 or No. 3) are shown in Table 2.

Comparative Examples 1 and 2

Organopolysiloxane compositions of Comparative Experiments (sample Nos. 9 and 10) were prepared according to the formulations shown in Table 2 by mixing phenylsilsesquioxane constituted solely by $T^{Ph}$ units and trimethylpentaphenyltrisiloxane at a weight ratio of 20:80 (Comparative Example 1) or at a weight ratio of 25:75 (Comparative Example 2) until uniform, using mechanical force (a mixer) at a temperature of 120° C. Evaluation results of the viscosity, refractive index, appearance immediately after preparation, and appearance after storage are shown for each sample in the Table.

Table 2: Liquid Aryl Group-Containing Polyorganosiloxane and Organopolysiloxane Compositions

TABLE 2

|  | Experimental Examples | | | | | |
| --- | --- | --- | --- | --- | --- | --- |
|  | Practical Example | | | | Comparative Example | |
|  | 2 | 3 | 7 | 8 | 1 | 2 |
| Sample No. | 2 | 3 | 7 | 8 | 9 | 10 |
| Formulation (parts by weight) | | | | | | |
| Sample No. 2 | 100 | | 20 | 20 | | |
| Sample No. 3 | | 100 | | | | |
| Phenylsilsesquioxane | | | | | 20 | 25 |
| (B) Trimethylpentaphenyltrisiloxane | | | 80 | 80 | 80 | 75 |

TABLE 2-continued

|  | Experimental Examples | | | | | |
|---|---|---|---|---|---|---|
|  | Practical Example | | | | Comparative Example | |
|  | 2 | 3 | 7 | 8 | 1 | 2 |
| <Physical Properties of Each Sample> | | | | | | |
| $Ph_2MeSiO_{1/2}$ units | 0.49 | 0.44 | 0.70 | 0.69 | 0.48 | 0.44 |
| $PhMeSiO_{2/2}$ units | 0.26 | 0.26 | 0.25 | 0.25 | 0.26 | 0.26 |
| $PhSiO_{3/2}$ units | 0.25 | 0.30 | 0.05 | 0.06 | 0.25 | 0.30 |
| Ph/Si mol | 1.47 | 1.44 | 1.63 | 1.62 | 1.47 | 1.44 |
| Viscosity (mPa·s) | 1,760 | 2,950 | 260 | 270 | 680 | 1,250 |
| Refractive index (25° C.) | 1.579 | 1.579 | 1.579 | 1.579 | 1.580 | 1.579 |
| Appearance immediately after manufacturing | Transparent | Transparent | Transparent | Transparent | Transparent | Transparent |
| Appearance after 1 month at 50° C. | Transparent | Transparent | Transparent | Transparent | Turbid | Turbid |

As shown in Table 1, the liquid aryl group-containing polyorganosiloxanes according to the present invention (sample Nos. 1 to 6) were colorless, transparent, uniform liquids having high refractive indices from about 1.58 to 1.60. Additionally, as shown in Tables 1 and 2, the liquid aryl group-containing polyorganosiloxanes or compositions thereof according to the present invention maintained a transparent appearance both immediately after manufacture and after being stored and white turbidity was not observed. Furthermore, while the composition according to the present invention likewise had an overall refractive index of about 1.58, samples could be prepared that had an overall composition viscosity at 25° C. of about 260 to 270. The viscosity of the composition is determined based on the mixing ratio of each of the components. Therefore, it is understood that a composition having a high refractive index could be easily prepared, said composition having at least a viscosity in a range from less than 260 mPa·s (low viscosity) to 12100 mPa·s, by selecting the component (A) from samples Nos. 1 to 6 (where the viscosity was from 1070 to 12100 mPa·s) and preparing at a mixing ratio with the component (B) other than at 20:80.

Figure 3:
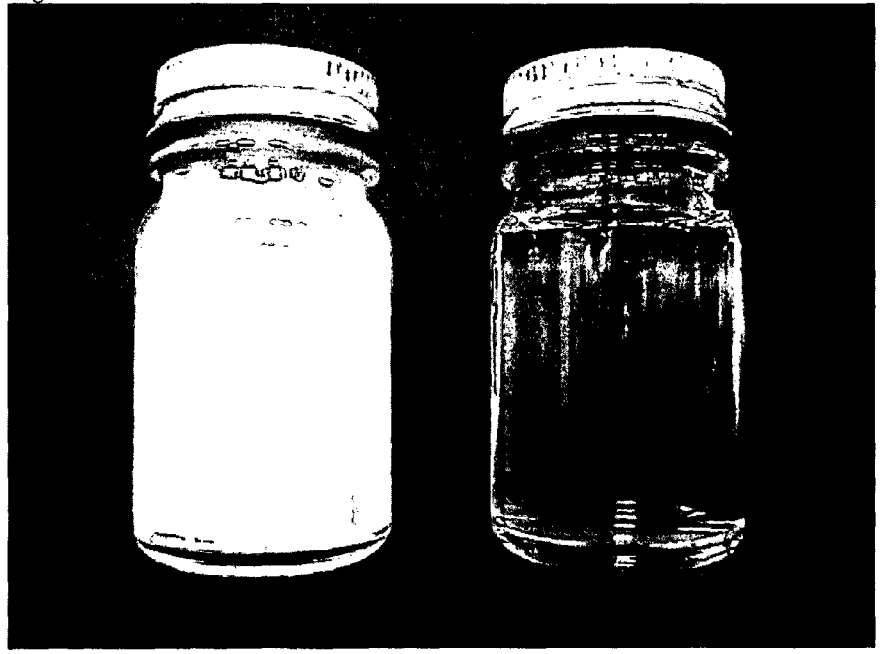
FIG. 3 is a photograph depicting changes in appearances (presence or absence of turbidity) of the composition of Comparative Example 2 (left) and the sample of Practical Example 3 (right, sample No. 3) after storing at 50° C. for one month.

On the other hand, with the organopolysiloxane compositions of the Comparative Experiments according to Comparative Examples 1 and 2, while the products were colorless, transparent liquids immediately after manufacture, the liquids became turbid over time. These samples correspond with the compositions described in Patent Document 6 (Japanese Unexamined Patent Application Publication No. 2011-136935). Exemplary test results are shown in FIG. 3, in which the appearance after storage of sample No. 3 (right) and the composition of Comparative Example 2 (left) are shown.

Practical Examples 9 and 10

Refractive Index of Composition Comprising the Liquid Aryl Group-Containing Polyorganosiloxane The refractive index of an organopolysiloxane composition obtained by mixing the liquid aryl group-containing polyorganosiloxane according to the present invention (sample No. 2 or sample No. 6) and various oil agents or oleophilic cosmetic raw materials (e.g. UV absorber) at a mixture ratio of 1:9 to 9:1 was measured at room temperature using an Abbe refractometer. Results thereof are shown below. Additionally, as Comparative Experiment (Comparative Example 3), the overall refractive index of compositions in cases where phenyl trimethicone (tradename: SH556, manufactured by Dow Corning Toray Co., Ltd.) is mixed with each of the components at the same ratio are shown in the table.

TABLE 3

Refractive index of the organopolysiloxane composition

| Component (oil agent or oleophilic cosmetic raw material) | Tradename | Practical Example 9 Liquid aryl group-containing polyorganosiloxane (sample No. 2) | | | Practical Example 10 Liquid aryl group-containing polyorganosiloxane (sample No. 6) | | | Comparative Example 3 Phenyl trimethicone (SH556) | | |
|---|---|---|---|---|---|---|---|---|---|---|
|  |  | Refractive index (mixture ratio = sample No. 2, sample No. 6, or SH556:each component) | | | | | | | | |
|  |  | 1:9 | 5:5 | 9:1 | 1:9 | 5:5 | 9:1 | 1:9 | 5:5 | 9:1 |
| Alkyl benzoate | Crodamol ™ AB (*1) | 1.4891 | 1.5246 | 1.5679 | 1.4986 | 1.5319 | 1.5810 | 1.4810 | 1.4715 | 1.4630 |
| Tri(capryl-capric acid)glyceryl | Crodamol ™ GTCC (*2) | 1.4581 | 1.5042 | 1.5658 | 1.4669 | 1.5128 | 1.5752 | 1.4500 | 1.4548 | 1.4590 |
| Ethylhexyl methoxycinnamate | UVINUL ® MC80N (*3) | 1.5459 | 1.5591 | 1.5748 | 1.5497 | 1.5670 | 1.5875 | 1.5361 | 1.5005 | 1.4690 |

TABLE 3-continued

Refractive index of the organopolysiloxane composition

| Component (oil agent or oleophilic cosmetic raw material) | Tradename | Practical Example 9 Liquid aryl group-containing polyorganosiloxane (sample No. 2) | | | Practical Example 10 Liquid aryl group-containing polyorganosiloxane (sample No. 6) | | | Comparative Example 3 Phenyl trimethicone (SH556) | | |
|---|---|---|---|---|---|---|---|---|---|---|
| | | Refractive index (mixture ratio = sample No. 2, sample No. 6, or SH556:each component) | | | | | | | | |
| | | 1:9 | 5:5 | 9:1 | 1:9 | 5:5 | 9:1 | 1:9 | 5:5 | 9:1 |
| Phenyl trimethicone | SH556 (*4) | 1.4698 | 1.5148 | 1.5640 | 1.4734 | 1.5175 | 1.5786 | — | | |

(*1): manufactured by Croda International, Plc.,
(*2): manufactured by Croda International, Plc.
(*3): manufactured by BASF,
(*4): manufactured by Dow Corning Toray Co., Ltd.

As shown in Table 3, in cases where the liquid aryl group-containing polyorganosiloxanes according to the present invention (samples No. 2 and No. 6) were mixed with the oil agent or the oleophilic cosmetic raw material described above, the refractive index was higher than that of the phenyl trimethicone (SH556). Particularly, when the mixture ratio of the samples No. 2 or No. 6 according to the present invention relative to each of the components was 50% or greater, a high refractive index of 1.50 or greater was maintained for all of the compositions.

Practical Examples 11 and 12

Compatibility of the Liquid Aryl Group-Containing Polyorganosiloxane and the UV Absorber Solubility when mixing the liquid aryl group-containing polyorganosiloxane (sample No. 2 or sample No. 6) and two types of UV absorbers (a UV-A region and UV-B region organic UV absorber, respectively) at various mixture ratios (from 1:9 to 9:1) was measured and evaluated according to the following standards.

Soluble: The silicone-based oil agent and the UV absorber blended uniformly.

Insoluble: A portion or all of the UV absorber did not dissolve in the silicone-based oil. Results of the evaluation are shown in Table 4. Additionally, for the purpose of providing Comparative Experiments in which other silicone-based oil agents are used, solubility was likewise evaluated using phenyl trimethicone (tradename: SH556, manufactured by Dow Corning Toray Co., Ltd.) or dimethicone (tradename: SH200-6cs, manufactured by Dow Corning Toray Co., Ltd.).

Table 4: Comparison of compatibility with the UV absorber (oleophilic cosmetic raw material)

TABLE 4

| Type of UV absorber | Practical Example 11 Liquid aryl group-containing polyorganosiloxane (sample No. 2) | | | Practical Example 12 Liquid aryl group-containing polyorganosiloxane (sample No. 6) | | | Comparative Example 4 Phenyl trimethicone (SH556) | | | Comparative Example 5 Dimethicone (SH200-6cs) | | |
|---|---|---|---|---|---|---|---|---|---|---|---|---|
| | Mixture ratio (silicane-based oil agent:UV absorber) | | | | | | | | | | | |
| | 1:9 | 5:5 | 1:9 | 1:9 | 5:5 | 1:9 | 1:9 | 5:5 | 1:9 | 1:9 | 5:5 | 1:9 |
| Ethylhexyl methoxycinnamate (tradename: UVINUL ® MC80N, manufactured by BASF) | Soluble | | | Soluble | | | Soluble | | | Insoluble | | |
| Diethylamino hydroxybenzoyl hexyl benzoate (tradename: UVINUL ® Aplus, manufactured by BASF) | Soluble | | | Soluble | | | Insoluble | Soluble | | Insoluble | | |

The two types of UV absorbers (a UV-A region and UV-B region organic UV absorber, respectively) dissolved uniformly, in a range from 1:9 to 9:1, in both of the liquid aryl group-containing polyorganosiloxanes according to the present invention (sample No. 2 and No. 6) so as to form a mixed composition. However, with the dimethicone (6cs) and the phenyl trimethicone, a uniform composition could not be obtained in cases when mixed with one or both of the UV absorbers, particularly when the compounding ratio of the diethylamino hydroxybenzoyl hexyl benzoate exceeded 50%. As such, it was confirmed that the liquid aryl group-containing polyorganosiloxanes according to the present invention (samples No. 2 and No. 6) have superior compatibility with oleophilic cosmetic raw materials.

Practical Examples 13 to 26

Cosmetic Compositions

Using the liquid aryl group-containing polyorganosiloxane according to the present invention, the following various cosmetic compositions having the following formulations were prepared and the characteristics of these compositions were evaluated according to the following test examples and evaluation standards. In the formulations, "liquid aryl group-containing polyorganosiloxane (No.)" indicates the liquid aryl group-containing polyorganosiloxane of the sample obtained in Practical Examples 1 to 6 that was used in the cosmetic composition formulation. Additionally, comparative cosmetic compositions were prepared according to the formulations shown in Tables 5 to 8. These cosmetic compositions, which correspond to the Practical Examples shown in the same Table, were also evaluated and results thereof were recorded.

Test examples and evaluation standards of the cosmetic compositions Depending on the type of cosmetic composition being evaluated, the following characteristics (1) to (8) were evaluated based on the standards listed below.
(1) Storage Stability
Products with the same appearance as the initial appearance after being stored at 50° C. for 1 month were indicated with an "○" symbol. Products in which separation over time was observed were indicated with an "x" symbol. Additionally, compositions that could not be emulsified were indicated by "x(*)" and "non-emulsifiable" was recorded outside of the table.
(2) Appearance
Products with overall uniformity in which oil separation and imbalances in pigment dispersion were absent were indicated by an "○" symbol. Non-uniform products were indicated by an "x" symbol.
(3) Film Thickness
A set amount of a rouge sample was applied to a glass slide. The appearance of the sample was visually examined for change immediately after application and after 1 hour.
<Evaluation Standards>
(Evaluation) ○: Has thickness and does not spread out; Δ: Spreads out some; x: Lacks thickness and spreads out greatly
(4) Retention
The cosmetic composition was applied to the skin. After 1 hour, the applied site was rinsed with water for 1 minute and retention of the cosmetic composition was visually observed.
<Evaluation Standards>
(Evaluation) ○: No change after rinsing; Δ: Some cosmetic composition remains; x: Most of the cosmetic composition does not remain (5) Shine
A dedicated panel of 10 people used each of the formulations and scored them (via sensory evaluation) on a 3-point scale. Evaluation scores arrived at by averaging the scores.
<Evaluation Standards>
1: No shine; 3: Normal shine; 5: Excellent shine
(Evaluation) ○: 4 or higher; Δ: from 2 to 4; x: 2 or less
(6) Spreadability
A dedicated panel of 10 people used each of the formulations and scored them (via sensory evaluation) on a 3-point scale. Evaluation scores arrived at by averaging the scores.
<Evaluation Standards>
1: No spreadability; 3: Normal spreadability; 5: Excellent spreadability
(Evaluation) ○: 4 or higher; Δ: from 2 to 4; x: 2 or less
(7) Skin Compatibility
A dedicated panel of 10 people used each of the formulations and scored them (via sensory evaluation) on a 3-point scale. Evaluation scores arrived at by averaging the scores.
<Evaluation Standards>
1: No compatibility; 3: Normal compatibility; 5: Excellent compatibility
(Evaluation) ○: 4 or higher; Δ: from 2 to 4; x: 2 or less
(8) Stickiness
A dedicated panel of 10 people used each of the formulations and scored them (via sensory evaluation) on a 3-point scale. Evaluation scores arrived at by averaging the scores.
<Evaluation Standards>
1: Stickiness felt; 3: Some stickiness felt; 5: No stickiness felt
(Evaluation) ○: 4 or higher; Δ: from 2 to 4; x: 2 or less Practical Example 13

Transparent Lipstick

A transparent lipstick was prepared using the components shown in Table 5 below. (all numbers are percentages by weight)

For comparison, formulations and evaluation results of products in which the liquid aryl group-containing polyorganosiloxane of the present invention (No. 1) was replaced with a different oil agent are shown as Comparative Example 6 and Comparative Example 7 in Table 5.

TABLE 5

Evaluation results of the transparent lipstick

| Formulation (wt. %) | | Practical Example 13 | Comparative Example 6 | Comparative Example 7 |
|---|---|---|---|---|
| Polyamide-modified silicone*1 | | 16.5 | 16.5 | 16.5 |
| Cyclohexasiloxane | | 33.0 | 33.0 | 33.0 |
| Isopropyl myristate | | 22.4 | 22.4 | 22.4 |
| Glyceryl tri (caprylate/caprate) | | 22.4 | 22.4 | 22.4 |
| Liquid aryl group-containing polyorganosiloxane (No. 1) | | 5.5 | | |
| Diisostearyl malate | | | 5.5 | |
| Dimethylsiloxane 500 cs | | | | 5.5 |
| Pearl pigment*2 | | 0.2 | 0.2 | 0.2 |
| Evaluation | Appearance | ○ | ○ | ○ |
| | Shine | ○ | ○ | Δ |
| | Retention | ○ | Δ | x |

*1 2-8178 Gellant, manufactured by Dow Corning
*2 RonaFlair Balance Red, manufactured by Merck Production Method The raw materials described above were heated, mixed, and uniformly blended. Thus, a transparent lipstick was obtained.

Evaluation Results

The obtained transparent lipstick was uniform overall, had a feeling of sheerness, and maintained an appearance with shine. On the other hand, the transparent lipsticks according to the Comparative Examples displayed scores for shine and retention that were inferior to those of the Practical Example.

Practical Example 14

W/O Sunscreen Cosmetic Composition

A W/O sunscreen cosmetic composition was prepared using the component shown in Table 6 below. (all numbers are percentages by weight)

For comparison, formulations and evaluation results of products in which the liquid aryl group-containing polyorganosiloxane of the present invention (No. 1) was replaced with a different oil agent are shown as Comparative Example 8 and Comparative Example 9 in Table 6.

TABLE 6

Evaluation results of the W/O sunscreen cosmetic composition

| Formulation (wt. %) | Practical Example 14 | Comparative Example 8 | Comparative Example 9 |
|---|---|---|---|
| a. Ethylhexyl methoxycinnamate | 5 | 5 | 5 |
| b. Diethylamino hydroxybenzoyl hexyl benzoate | 2 | 2 | 2 |
| c. Liquid aryl group-containing polyorganosiloxane (No. 1) | 3 | | |
| d. Phenyl-modified silicone*1 | | 3 | |
| e. Dimethicone 500 cs | | | 3 |
| f. Alkyl-modified silicone*2 | 10 | 10 | 10 |
| g. Polyether-modified silicone*3 | 2 | 2 | 2 |
| h. Sodium chloride | 1 | 1 | 1 |
| i. Butylene glycol | 5 | 5 | 5 |
| j. Water | 72 | 72 | 72 |
| k. Preservative | q.s. | q.s. | q.s. |
| Evaluation Storage stability (at 50° C. for 1 month) | ○ | ○ | x(*) |
| Retention | ○ | Δ | — |
| Skin compatibility | ○ | Δ | — |

*1SH556, manufactured by Dow Corning Toray Co., Ltd.
*2FZ-3196, manufactured by Dow Corning Toray Co., Ltd.
*3ES-5612 formulation aid, manufactured by Dow Corning Toray Co., Ltd.
x(*): Not evaluated due to being unable to emulsify Production Method 1. Components a to g were blended until uniform. (Component 1)
2. Components h to k were blended until uniform. (Component 2)
3. Component 2 was added in small portions to component 1 and the mixture was emulsified.

Evaluation Results

The obtained W/O sunscreen cosmetic composition had superior storage stability after emulsification and superior on-skin sensory evaluation results. On the other hand, the on-skin sensory evaluation results of the W/O sunscreen cosmetic composition according to Comparative Example 8 were inferior and the formulation according to Comparative Example 9 could not be emulsified.

Practical Examples 15 and 16

Liquid Rouges

Figure 4:
FIG. 4 is a photograph depicting the gloss and luster of the liquid rouge of Practical Example 15 (right) and the liquid rouge of Comparative Example 10 (left) when applied on a glass slide.

Liquid rouges were prepared using the components shown in Table 7 below. (all numbers are percentages by weight) For comparison, formulations and evaluation results of products in which the liquid aryl group-containing polyorganosiloxane of the present invention was replaced with phenyl trimethicone and in which the liquid aryl group-containing polyorganosiloxane of the present invention was not added are shown as Comparative Example 10 and Comparative Example 11 in Table 7. FIG. 4 is a photograph depicting 0.5 g of each of the liquid rouges of Practical Example 15 and Comparative Example 10, applied on a glass slide.

TABLE 7

Evaluation results of the liquid rouges

| Formulation (wt. %) | Practical Example 15 | Practical Example 16 | Comparative Example 10 | Comparative Example 11 |
|---|---|---|---|---|
| Heavy liquid isoparaffin | 40 | 40 | 40 | 40 |
| Diisostearyl malate | 10 | 10 | 10 | 10 |
| Squalane | 10 | 10 | 10 | 10 |
| Dextrin palmitate*1 | 3 | 3 | 3 | 3 |
| Petrolatum | 10 | 10 | 10 | 10 |
| Iron oxide | 0.5 | 0.5 | 0.5 | 0.5 |
| Red No. 202 | 0.5 | 0.5 | 0.5 | 0.5 |
| Pearl pigment*2 | 3 | 3 | 3 | 3 |
| Diglyceryl diisostearate | 2 | 2 | 2 | 2 |
| Silica silylate*3 | 1 | 1 | 1 | 1 |
| Liquid aryl group-containing polyorganosiloxane (No. 2) | 20 | | | |
| Liquid aryl group-containing polyorganosiloxane (No. 6) | | 20 | | |
| Phenyl-modified silicone*4 | | | 20 | |
| Evaluation Appearance | ○ | ○ | x | Δ |
| Shine | ○ | ○ | ○ | ○ |
| Spreadability | ○ | ○ | ○ | Δ |
| Film thickness | ○ | ○ | x | Δ |
| Retention | ○ | ○ | x | x |
| Note (FIG. 4): Photograph of 0.5 g of product applied | Right | — | Left | — |

*1Rheopearl KL, manufactured by Chiba Flour Milling Co., Ltd.
*2RonaFlair Balance Red, manufactured by Merck
*3VM-2270, manufactured by Dow Corning Toray Co., Ltd.
*4SH556, manufactured by Dow Corning Toray Co., Ltd.

Production Method

The components were heated at 85° C. and uniformly mixed according to the formulations shown in the Table. Thus, liquid rouges were obtained.

Evaluation Results

The obtained liquid rouges had superior appearance, shine, tactile sensation (spreadability), film thickness, and retention. Particularly, as shown in FIG. 4, compared to cases where the phenylmethicone (SH556) was compounded (FIG. 4, left) and the like, with the Practical Examples, a thickly textured result with the same application amount was achieved (FIG. 4, right). On the other hand, particularly from the perspectives of appearance, retention, and film thickness, the liquid rouges according to Comparative Examples 10 and 11 were inferior to the Practical Examples of the present invention.

Practical Example 17

Lipstick

A lipstick was prepared using the components shown in Table 8 below. (all numbers are percentages by weight)

For comparison, a formulation and evaluation results of a product in which the liquid aryl group-containing polyorganosiloxane of the present invention (No. 2) was replaced with a heavy liquid isoparaffin are shown as Comparative Example 12 in Table 8.

TABLE 8

Evaluation results of the lipsticks

| Formulation (wt. %) | Practical Example 17 | Comparative Example 12 |
|---|---|---|
| Liquid aryl group-containing polyorganosiloxane (No. 2) | 40 | |
| Heavy liquid isoparaffin | | 40 |
| Glyceryl triisostearate | 30 | 30 |
| Paraffin wax | 11 | 11 |
| Microcrystalline wax | 6.6 | 6.6 |
| Candelilla wax | 1.2 | 1.2 |
| Polyethylene wax | 1.4 | 1.4 |
| Red No. 201 | 1 | 1 |
| Iron oxide | 1 | 1 |
| Red No. 202 | 0.5 | 0.5 |
| Pearl pigment*1 | 2.3 | 2.3 |
| Carbinol-modified silicone*2 | 5 | 5 |
| Evaluation  Appearance | ○ | ○ |
| Shine | ○ | Δ |
| Spreadability | ○ | x |
| Stickiness | ○ | x |
| Retention | ○ | ○ |

*1RonaFlair Balance Red, manufactured by Merck
*25562 carbinol fluid, manufactured by Dow Corning Toray Co., Ltd.

Production Method

The raw materials described above were heated, mixed, and uniformly blended. Thus, a lipstick was obtained.

Evaluation Results

The obtained lipstick was uniform overall and maintained an appearance with shine. On the other hand, the lipstick according to the Comparative Example displayed scores for shine, spreadability, and stickiness, that were inferior to those of the Practical Example.

Practical Example 18

Eye Shadow

An eye shadow was prepared consisting of the following components. (all numbers are percentages by weight)

| | |
|---|---|
| (1) Polyether-modified silicone*1 | 10 |
| (2) Cyclopentasiloxane | 15 |
| (3) Acryl-modified silicone*2 | 30 |
| (4) Phenyl-modified silicone*3 | 7.5 |
| (5) Liquid aryl group-containing polyorganosiloxane (No. 1) | 14.5 |
| (6) Water | 2 |
| (7) Red No. 202 | 1 |
| (8) Blue No. 1 | 0.35 |
| (9) Titanium oxide | 0.65 |
| (10) Carbinol-modified silicone*4 | 2 |
| (11) Silicone elastomer powder*5 | 6 |
| (11) Pearl pigment*6 | 10 |

*1BY11-030, manufactured by Dow Corning Toray Co., Ltd.
*2FA 4001 CM, manufactured by Dow Corning Toray Co., Ltd.
*3SH556, manufactured by Dow Corning Toray Co., Ltd.
*45562 carbinol fluid, manufactured by Dow Corning Toray Co., Ltd.
*59701 cosmetic powder, manufactured by Dow Corning Toray Co., Ltd.
*6Timiron ® Super Blue, manufactured by Merck Production Method
1. Uniformly mix components (1) to (5) at room temperature.
2. Add component (6) in small portions to the mixture while mixing at high speed. Blend uniformly.
3. Add components (7) to (10) and mix until uniform.
4. Add components (11) and (12) and mix until uniform.

Evaluation Results

An eye shadow product having superior shine and luster, and that was uniform throughout, was obtained via the formulation described above.

Practical Example 19

Blush

A blush was prepared using the following components. (all numbers are percentages by weight)

| | |
|---|---|
| (1) Pigment*1 | 19 |
| (2) Mica | 6.5 |
| (3) Pearl pigment*2 | 11.5 |
| (4) Silicone elastomer powder*3 | 5 |
| (5) Liquid aryl group-containing polyorganosiloxane (No. 1) | 15.5 |
| (6) Liquid aryl group-containing polyorganosiloxane (No. 2) | 41.5 |

*1Colorona ® Red Brown, manufactured by Merck.
*2Timiron ® Super Red, manufactured by Merck.
*39701 cosmetic powder, manufactured by Dow Corning Toray Co., Ltd.

Production Method
1. Uniformly mix components (1) to (4).
2. Then add components (4) and (5) and mix until uniform.

Evaluation Results

The overall form of the obtained blush was a uniform mousse, and this form was stably maintained for more than one month.

Practical Example 20

Mascara (Emulsion Type)

A W/O emulsion-type mascara was prepared consisting of the following components. (all numbers are percentages by weight)

| | |
|---|---|
| (1) Polyether-modified silicone*1 | 10 |
| (2) Carbon black | 25 |
| (3) Silicone elastomer*2 | 10 |
| (4) Dimethylpolysiloxane 2cs | 10 |
| (5) Acryl-modified silicone*3 | 9 |
| (6) Liquid aryl group-containing polyorganosiloxane (No. 3) | 4.3 |
| (7) Isododecane | 6.7 |
| (8) Water | 23 |
| (9) Sodium chloride | 2 |
| (10) Preservative | q.s. |

*1BY22-008M, manufactured by Dow Corning Toray Co., Ltd.
*2EL-8050ID silicone organic elastomer blend, manufactured by Dow Corning Toray Co., Ltd.
*3FA 4002 ID, manufactured by Dow Corning Toray Co., Ltd.

Production Method
1. Mix components (1) and (2).
2. Mix components (3) to (7).
3. Add 2 to 1 while mixing at high speed and blend.
4. Mix components (8) to (10).
5. Add 4 to 3 while mixing at high speed and emulsify.

Evaluation Results

An emulsion-type mascara product that was uniform throughout was obtained via the formulation described above.

Practical Example 21

Eye Liner (Gel)

An eye liner was prepared consisting of the following components. (all numbers are percentages by weight)

| | |
|---|---|
| (1) Silicone resin wax*[1] | 10 |
| (2) Silicone elastomer powder*[2] | 2 |
| (3) Glyceryn stearate | 2 |
| (4) Silica silylate*[3] | 4 |
| (5) Carbon black | 8 |
| (6) Isododecane | 25 |
| (7) MQ resin*[4] | 15 |
| (8) Isododecane | 26 |
| (9) Liquid aryl group-containing polyorganosiloxane (No. 4) | 8 |

*[1]SW-8005 C30 Resin Wax, manufactured by Dow Corning Toray Co., Ltd.
*[2]9701 Cosmetic Powder, manufactured by Dow Corning Toray Co., Ltd.
*[3]VM-2270 Aerogel Fine Particles, manufactured by Dow Corning Toray Co., Ltd.
*[4]MQ-1640 Solid Resin, manufactured by Dow Corning Toray Co., Ltd.

Production Method
1. Mix components (1) to (6) at 75° C.
2. Mix components (7) to (9) at 75° C.
3. Add 2 to 1 while mixing and blend until uniform.
4. Cool while mixing.

Evaluation Results

A gel eye liner that was uniform throughout was obtained via the formulation described above.

Practical Example 22

Hair Styling Agent (O/W Emulsion-Type)

A hair styling agent was prepared using the following components. (all numbers are percentages by weight)

| | |
|---|---|
| (1) Polyether-modified silicone*[1] | 2 |
| (2) Water | 48.3 |
| (3) Glycerin | 2 |
| (4) Amino elastomer emulsion*[2] | 6.7 |
| (5) Liquid aryl group-containing polyorganosiloxane (No. 1) | 3 |
| (6) Phenyl-modified silicone*[3] | 3 |
| (7) Polyoxyethylene glycerine fatty acid ester*[4] | 20 |
| (8) Cetearyl alcohol | 15 |
| (9) Preservative | q.s. |

*[1]SH3771M, manufactured by Dow Corning Toray Co., Ltd.
*[2]CE-7080 Smart Style, manufactured by Dow Corning Toray Co., Ltd.
*[3]SH556, manufactured by Dow Corning Toray Co., Ltd.
*[4]GLYCEROX HE, manufactured by Croda International, Plc.

Production Method
1. Heat and dissolve components (1) to (4) at 70° C.
2. Heat and dissolve components (5) to (8) at 70° C.
3. Add 2 to 1 in small portions while mixing and emulsify.
4. Cool while mixing.
5. Add component (9) and mix until uniform.

Evaluation Results

A hair styling agent was obtained via the formulation described above.

Practical Example 23

Foundation (Liquid Type)

A liquid foundation was prepared consisting of the following components. (all numbers are percentages by weight)

| | |
|---|---|
| (1) Polyether-modified silicone*[1] | 4 |
| (2) Silicone elastomer*[2] | 5 |
| (3) Alkyl-modified silicone*[3] | 3 |
| (4) Glyceryl tri(caprylate/caprate) | 2 |
| (5) Liquid aryl group-containing polyorganosiloxane (No. 1) | 2 |
| (6) Phenyl-modified silicone*[4] | 3.35 |
| (7) Hydrophobization-treated iron oxide yellow*[5] | 0.4 |
| (8) Hydrophobization-treated iron oxide red*[6] | 0.17 |
| (9) Hydrophobization-treated iron oxide black*[7] | 0.08 |
| (10) Titanium oxide | 6 |
| (11) Glycerin | 15 |
| (12) Sodium chloride | 1 |
| (13) Water | bal. |
| (14) Preservative | q.s. |

*[1]ES-5300 Formulation Aid, manufactured by Dow Corning Toray Co., Ltd.
*[2]EL-8050ID Silicone Organic Elastomer Blend, manufactured by Dow Corning Toray Co., Ltd.
*[3]SS-3408, manufactured by Dow Corning Toray Co., Ltd.
*[4]SH556, manufactured by Dow Corning Toray Co., Ltd.
*[5]SA-IOY-8, manufactured by Miyoshi Kasei, Inc.
*[6]SA-IOR, manufactured by Miyoshi Kasei, Inc.
*[7]SA-IOB, manufactured by Miyoshi Kasei, Inc.

Production Method
1. Mix components (1) to (5).
2. Mix components (6) to (10).
3. Mix 1 and 2 until uniform.
4. Mix components (11) to (13).
5. Add 4 to 3 in small portions while mixing and emulsify.
6. Add component (14) and mix until uniform.

Evaluation Results

A liquid foundation was obtained via the formulation described above.

Practical Example 24

O/W Sunscreen (Cream Type)

An O/W sunscreen was prepared consisting of the following components. (all numbers are percentages by weight)

| | |
|---|---|
| (1) Silicone emulsifier premix*[1] | 10 |
| (2) Polyoxyethylene alkyl ether phosphate*[2] | 0.05 |
| (3) Ethylhexyl methoxycinnamate | 5 |
| (4) Diethylamino hydroxybenzoyl hexyl benzoate | 2 |
| (5) Liquid aryl group-containing polyorganosiloxane (No. 2) | 3 |
| (6) Water | 40 |
| (7) Carbomer (2% aqueous solution) | 22.5 |
| (8) Sodium hydroxide (1% aqueous solution) | 10.5 |
| (9) Butylene glycol | 7 |
| (10) Preservative | q.s. |

*[1]FB-2540, manufactured by Dow Corning Toray Co., Ltd.
*[2]Hostaphat KL340D, manufactured by Clariant Production Method
1. Mix components (1) to (5) until uniform.
2. Mix components (6) to (10) until uniform.
3. Add 1 to 2 while mixing and emulsify.

Evaluation Results

An O/W sunscreen was obtained via the formulation described above.

Practical Example 25

Lipstick

A lipstick was prepared consisting of the following components. (all numbers are percentages by weight)

| | | |
|---|---|---|
| (1) | Carbinol-modified silicone*[1] | 26 |
| (2) | Red No. 201 | 0.6 |
| (3) | Red No. 202 | 0.6 |
| (4) | Pearl pigment*[2] | 9 |
| (5) | Candelilla wax | 8 |
| (6) | Beeswax | 4 |
| (7) | Carnauba wax | 1.5 |
| (8) | Propylparaben | 0.2 |
| (9) | Petrolatum | 2 |
| (10) | Phenyl-modified silicone*[3] | 6 |
| (11) | Liquid aryl group-containing polyorganosiloxane (No. 2) | 6 |
| (12) | Acryl-modified silicone*[4] | 12 |
| (13) | Jojoba oil | 3.5 |
| (14) | Glyceryl tri (caprylate/caprate) | 20.6 |

*[1]5562 Carbinol Fluid, manufactured by Dow Corning Toray Co., Ltd.
*[2]Timiron ® Supersheen MP-1001, manufactured by Merck
*[3]SH556, manufactured by Dow Corning Toray Co., Ltd.
*[4]FA4001CM, manufactured by Dow Corning Toray Co., Ltd.

Production Method
1. Mix components (1) to (4) until uniform.
2. Mix components (5) to (9) at 80° C. until uniform.
3. Add 1 to 2 while mixing and blend at 80° C.
4. Add components (10) to (14) to 3 and mix at 80° C.
5. Pour the mixture into a container.

Evaluation Results

A lipstick was obtained via the formulation described above.

Practical Example 26

Rouge (Palette-Type)

A rouge was prepared consisting of the following components. (all numbers are percentages by weight)

| | | |
|---|---|---|
| (1) | Isododecane | 39 |
| (2) | Liquid aryl group-containing polyorganosiloxane (No. 1) | 9 |
| (3) | Silicone resin*[1] | 15 |
| (4) | Dimethyl silicone 2cs | 17 |
| (5) | Red No. 201 | 1 |
| (6) | Iron oxide | 1 |
| (7) | Red No. 202 | 0.5 |
| (8) | Titanium oxide | 0.5 |
| (9) | Dimethicone 2cs | 3 |
| (10) | Pearl pigment*[2] | 2 |
| (11) | Silica silylate*[3] | 5 |
| (12) | Silicone rubber powder*[4] | 2 |
| (13) | Beeswax | 5 |

*[1]MQ-1640 Flake Resin, manufactured by Dow Corning Toray Co., Ltd.
*[2]Timiron ® Supersheen MP-1001, manufactured by Merck
*[3]VM-2270 Aerogel Fine Particles, manufactured by Dow Corning Toray Co., Ltd.
*[4]9701 Cosmetic Powder, manufactured by Dow Corning Toray Co., Ltd.

Production Method
1. Mix components (1) to (4) until uniform.
2. Mix components (5) to (9) until uniform.
3. Add 1 to 2 and mix.
4. Add components (10) to (12) to 3 and heat at 80° C.
5. Dissolve component (13) at 80° C., add to 4, and mix.
6. Cool while mixing until the temperature is 45° C.
7. Pour the mixture into a compact.

Evaluation Results

A rouge that was uniform throughout was obtained via the formulation described above.

Practical Example 27

Skin Cream

A skin cream for concealing pores was prepared consisting of the following components. (all numbers are percentages by weight)

TABLE 9

Figure 5:
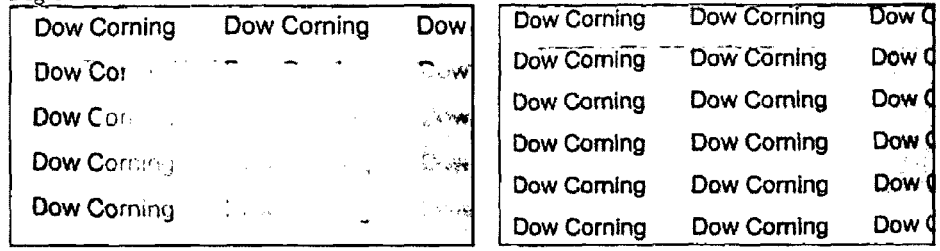
FIG. 5 is a photograph depicting the soft focus effects of the composition of Practical Example 26 (left) and the composition of Comparative Example 13 when applied on a glass slide.

| | | Practical Example 27 | Comparative Example 13 |
|---|---|---|---|
| (1) | Silicone emulsifier premix*1 | 3 | 3 |
| (2) | Purified water | 68.2 | 68.2 |
| (3) | Liquid aryl group-containing polyorganosiloxane (No. 2) | 18 | — |
| (4) | Dimethylsiloxane 6cs | — | 18 |
| (5) | Isododecane | 1.8 | 1.8 |
| (6) | Silicone elastomer*2 | 9 | 9 |
| | Photograph of FIG. 5 | Left (soft focus observed) | Right (no soft focus) |

*1RM2051, manufactured by Dow Corning Toray Co., Ltd.
*2EP-9215 Cosmetic Powder, manufactured by Dow Corning Toray Co., Ltd.

Production Method
1. Add component (2) in small amounts to component (1) while mixing and emulsify.
2. Add and disperse components (3) to (6) in the emulsion of 1 while stirring. Thus, a cream for concealing pores was obtained.

Evaluation Results

The obtained composition was applied to a glass slide so that the nonvolatile component had a thickness of 10 microns. Then, the glass slide was placed on a piece of paper on which characters were written and the visibility of the characters was visually observed. As a result, as shown in Table 9 and FIG. 5, the characters (Dow Corning) of Practical Example 26 appeared blurry. From this result, it is clear that the liquid aryl group-containing polyorganosiloxane of the present invention had pore concealing (soft focus) effects when combined with a silicone elastomer powder that were superior than those of a low refractive index dimethyl silicone.

Practical Example 28

Emulsion

An emulsion was prepared consisting of the following components. (all numbers are percentages by weight)

TABLE 10

| Component | Practical Example 28 | Comparative Example 14 |
|---|---|---|
| (1) Polyether-modified silicone*1 | 2 | 2 |
| (2) Dimethylpolysiloxane*2 | 4 | 4 |
| (3) Phenyl-modified silicone*3 | 2 | 2 |
| (4) Isopropyl myristate | 2 | 2 |
| (5) Glyceryl tri(caprylate/caprate) | 2 | 2 |
| (6) Cyclopentasiloxane | 13.5 | 14 |
| (7) Rice oil | 2 | 2 |
| (8) Liquid aryl group-containing polyorganosiloxane (No. 4) | 0.5 | — |
| (9) Purified water | bal. | bal. |
| (10) Sodium chloride | 1 | 1 |
| (11) Ethanol | 9 | 9 |
| (12) Glycerin | 3 | 3 |

TABLE 10-continued

| Component | Practical Example 28 | Comparative Example 14 |
|---|---|---|
| (13) Preservative | q.s. | q.s. |
| Criterion: Skin compatibility (Evaluation results of the dedicated panelists) | ○ | x |

*1FZ-2233, manufactured by Dow Corning Toray Co., Ltd.
*22-1184 Fluid, manufactured by Dow Corning Toray Co., Ltd.
*3SH556, manufactured by Dow Corning Toray Co., Ltd.

Production Method

1. Mix components (1) to (8) at room temperature until uniform.
2. Mix components (9) to (13) at room temperature until uniform.
3. Add mixture 2 in small portions to the mixture 1 while mixing at high speed, and emulsify.

Evaluation Method

Skin Compatibility

A dedicated panel of 10 people used each of the formulations and scored them (via sensory evaluation) on a 3-point scale. Evaluation scores arrived at by averaging the scores.

<Evaluation Standards>

1: No compatibility; 3: Normal compatibility; 5: Excellent compatibility (Evaluation) ○: 4 or higher; Δ: from 2 to 4; x: 2 or less As shown in Table 10, compared to the Comparative Example, the emulsion according to the present invention scored higher in the sensory evaluation criterion of skin compatibility. From this, it is clear that the emulsion according to the present invention has superior sensation during use.

Practical Example 29

Powder Foundation

A powder foundation was prepared consisting of the following components. (all numbers are percentages by weight)

TABLE 11

Figure 6:
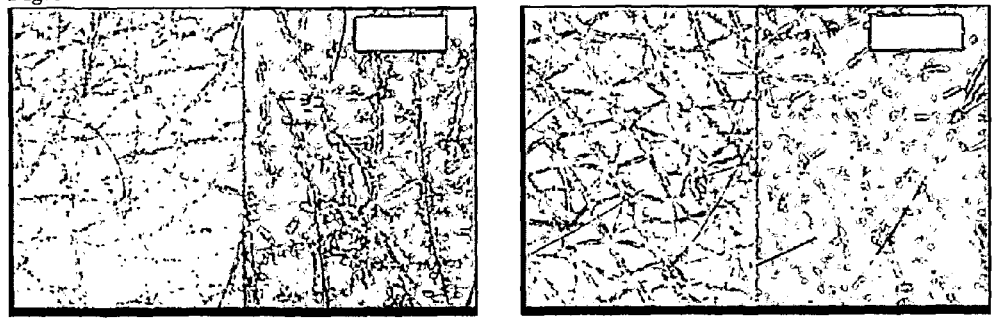
FIG. 6 is a photograph depicting results of observations using a microscope of the skin surface after applying the foundation of Practical Example 29 (right) and the foundation of Comparative Example 15 (left) on the skin.

| Component | Practical Example 29 | Comparative Example 15 |
|---|---|---|
| (1) Talc*1 | 9.1 | 9.1 |
| (2) Titanium oxide*2 | 8.8 | 8.8 |
| (3) Mica*3 | 48.4 | 48.4 |
| (4) Acrylic powder*4 | 10.56 | 10.56 |
| (5) Fine particulate titanium oxide*5 | 4.4 | 4.4 |
| (6) Silicone treated yellow iron oxide | 1.76 | 1.76 |
| (7) Silicone treated red iron oxide | 0.35 | 0.35 |
| (8) Silicone treated black iron oxide | 0.14 | 0.14 |
| (9) Hydroxyapatite *6 | 4.4 | 4.4 |
| (10) Methylparaben | 0.09 | 0.09 |
| (11) Dimethylpolysiloxane (20cs) | 3.29 | 3.29 |
| (12) Liquid aryl group-containing polyorganosiloxane (No. 4) | 3.3 | — |
| (13) Dimethylpolysiloxane (5000cs) | — | 3.3 |
| (14) Neopentylglycol dioctanoate | 1.2 | 1.2 |
| (15) Squalane | 3.59 | 3.59 |
| (16) Di(octyldodecyl/phytosteryl/behenyl)lauroyl glutamate | 0.6 | 0.6 |
| (17) Tocopherol | 0.01 | 0.01 |
| (18) Propylparaben | 0.01 | 0.01 |
| Criterion: Natural feel when applied (Evaluation results of the dedicated panelists) | ○ | x |
| Photograph of FIG. 6 | Right | Left |

*1Talc DN-SH, manufactured by Dainihon Kasei Co., Ltd.
*2Titanium DN-SH (2), manufactured by Dainihon Kasei Co., Ltd.
*3A 2:1 mixture of hydrogen dimethicone treated SA-Sericite FSE (manufactured by Miyoshi Kasei, Inc.) and hydrogen dimethicone treated Mica Y-2300 (manufactured by Yamaguchi Mica Co., Ltd.)
*4Matsumoto Microsphere M-100, manufactured by Matsumoto Yushi-Seiyaku Co., Ltd.
*5TTO-55C, manufactured by Ishihara Sangyo Kaisha, Ltd.
*6: HAP-SC, manufactured by Taihei Chemical Industrial Co., Ltd.

Production Method

1. Uniformly mix components (1) to (10), and then process using a pulverizer.
2. Heat and dissolve components (11) to (18), and then cool to room temperature.
3. Add the mixture 2 to the mixture 1 and mix. Then pulverize the entire mixture using a pulverizer.
4. Use a filter to gather all particles of like sizes. Then, pour the mixture into a compact and compression-mold.

Evaluation Method

Natural Feel when Applied

A dedicated panel of 10 people used each of the formulations and scored them (via sensory evaluation) on a 3-point scale. Evaluation scores arrived at by averaging the scores.

<Evaluation Standards>

1: Compared to bare skin, white flaking is noticeable; 3: Slightly noticeable compared to bare skin; 5: Compared to bare skin, no white flaking is noticeable (Evaluation) ○: 4 or higher; Δ: from 2 to 4; x: 2 or less Additionally, the obtained foundation was taken up in a sponge and applied to the skin. Then, the surface of the skin was observed under a microscope (Video Microscope VL-7EXII, manufactured by Scalar Corporation). As a result, it was found that, compared to Comparative Example 15 in which dimethylpolysiloxane having a viscosity of 5000 cs was used, the foundation of Practical Example 29 was less noticeable when present in pores and wrinkles. This indicates that, because the refractive index of the liquid aryl group-containing polyorganosiloxane (No. 4) according to the present invention is higher than that of dimethylpolysiloxane, the difference in refractive indices of titanium oxide and similar high refractive index powders is small and, in cases when applied to the skin, the foundation has a feeling of sheerness and superior effects of concealing wrinkles.

Practical Example 30

Pigment Premix for Foundations

A pigment premix slurry for foundations was prepared consisting of the following components. (all numbers are percentages by weight)

TABLE 12

| Component | Practical Example 30 | Comparative Example 16 |
|---|---|---|
| Pigment titanium oxide*1 | 29 | 29 |
| Mica*2 | 16 | 16 |
| Silicone treated yellow iron oxide*3 | 4 | 4 |
| Silicone treated red iron oxide*4 | 1 | 1 |
| Silicone treated black iron oxide*5 | 0.06 | 0.06 |

TABLE 12-continued

Figure 7:
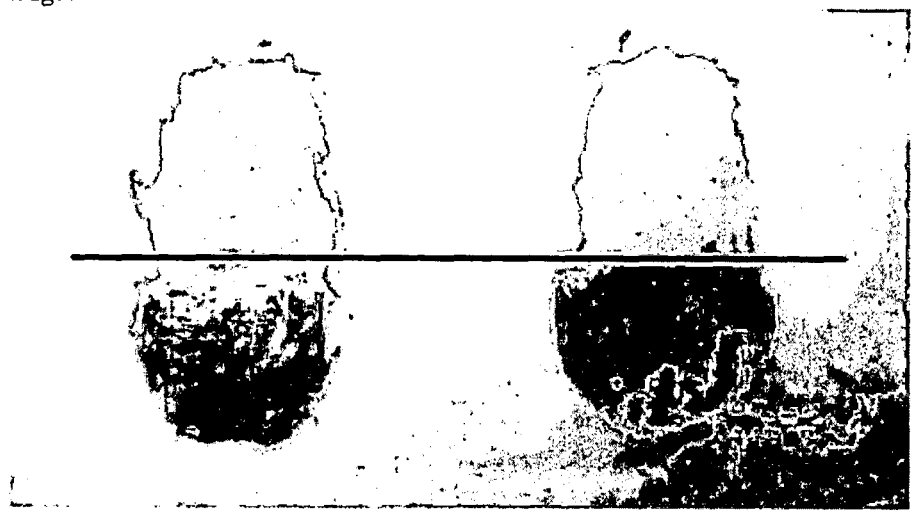
FIG. 7 is a photograph in which the pigment premix slurry of Practical Example 30 (left) and the pigment premix slurry of Comparative Example 16 (right) are applied on a PET film. This photograph depicts color variation when ethylhexyl methoxycinnamate is dripped on a lower portion (below the black line) and mixed with the pigment premix slurries using a spatula.

| Component | Practical Example 30 | Comparative Example 16 |
|---|---|---|
| Liquid aryl group-containing polyorganosiloxane (No. 4) | 50 | |
| Diisostearyl malate | | 50 |
| FIG. 7: Ethylhexyl methoxycinnamate was applied on the portion under the black line and changes in color from the portion above the black line were observed. Results are as shown to the right: | Left: No change in color (identical) | Right: Change in color (darkened) |

*1SA Titanium CR-50, manufactured by Miyoshi Kasei, Inc.
*2SA Excel Mica JP-2, manufactured by Miyoshi Kasei, Inc.
*3SA Yellow UXLO, manufactured by Miyoshi Kasei, Inc.
*4SA Red, manufactured by Miyoshi Kasei, Inc.
*5SA Black, manufactured by Miyoshi Kasei, Inc.

Production Method

All components were mixed until uniform. Thus, a pigment premix slurry for foundations was prepared.

Evaluation Method

The obtained pigment premix slurry was spread on a PET film. Ethylhexyl methoxycinnamate was applied dropwise on the portion under the black line and mixed with the pigment premix slurry. After five minutes, changes in color between the portion above and the portion below the black line were visually confirmed.

As shown in Table 12 and FIG. 7, compared with Practical Example 30 in which there was no change in color, darkening of the color of Comparative Example 16 was seen. This suggests that coloration can be easily adjusted by pre-mixing a pigment with the liquid aryl group-containing polyorganosiloxane of the present invention and preventing changes in color.

Practical Example 31

Frizz-Control Hair Treatment Composition

A frizz-control hair treatment composition was prepared consisting of the following components. (all numbers are percentages by weight)

TABLE 13

| Component (INCI name) | Practical Example 31 | Comparative Example 17 |
|---|---|---|
| Phase A | | |
| C12-15 Alkyl Benzoate | 10 | 14 |
| Trideceth | 0.5 | 0.5 |
| Liquid aryl group-containing polyorganosiloxane (No. 4) | 4.00 | — |
| Phase B | | |
| Water | 81.30 | 81.30 |
| Hydroxyethyl Acrylate/Sodium Acryloyldimethyl Taurate Copolymer | 1.00 | 1.00 |
| Glycerin | 3.00 | 3.00 |
| Phenoxyethanol and Ethylhexylglycerin | 0.20 | 0.20 |

Production Method

Mix ingredients of phase A together until homogeneous.
Mix ingredients of phase B together until homogeneous.
Add phase A to phase B with medium mixing shear, and mix them until homogeneous.
Thus, a hair treatment composition was prepared.

Evaluation Method

Hair tresses are pre-washed and then treated with formulations to be evaluated. After treatment, hair tresses are blow dried to be straightened. Picture of the tress is taken and is recorded as Time=0 picture. Tresses are then placed in humidity chamber for 1.5 hours (=90 minutes) under controlled temperature and humidity, respectively 25° C. and 80% relative humidity. Pictures are taken at set times: 0, 10, 20, 30, 45 and 90 min for each treated tresses. Pictures are then analyzed with a image analysis software, two indexes are calculated and recorded in table 14 and 15 (see next section): respectively frizz index and aspect ratio. 6 tresses are used per treatment type. Frizz index quantifies the frizziness of hair tress. Aspect ratio of a tress is the ratio tress width over tress length.

TABLE 14

Frizz index of treated hair tresses

| Hair treatment | | Practical Example 31 | | Comparative Example 17 | |
|---|---|---|---|---|---|
| | | Average | Standard deviation | Average | Standard deviation |
| Frizz Index | 0 | 43.33 | 12.38 | 87.09 | 49.40 |
| | 10 | 104.45 | 48.71 | 264.54 | 54.65 |
| | 20 | 152.62 | 63.30 | 348.67 | 63.73 |
| | 30 | 187.22 | 77.17 | 413.33 | 60.67 |
| | 45 | 214.83 | 87.31 | 471.10 | 63.23 |
| | 60 | 239.12 | 94.18 | 500.84 | 57.83 |
| | 90 | 263.90 | 100.87 | 514.80 | 51.75 |

TABLE 15

Aspect Ratio of treated hair tresses

| Hair treatment | | Practical Example 31 | | Comparative Example 17 | |
|---|---|---|---|---|---|
| | | Average | Standard deviation | Average | Standard deviation |
| Aspect Ratio | 0 | 0.12 | 0.01 | 0.16 | 0.01 |
| | 10 | 0.22 | 0.03 | 0.30 | 0.04 |
| | 20 | 0.28 | 0.05 | 0.39 | 0.03 |
| | 30 | 0.31 | 0.06 | 0.43 | 0.04 |
| | 45 | 0.35 | 0.06 | 0.47 | 0.05 |
| | 60 | 0.37 | 0.06 | 0.50 | 0.05 |
| | 90 | 0.39 | 0.06 | 0.50 | 0.05 |

As shown in Table 14 and Table 15, hair tresses treated with hair treatment of practical example 31 kept lower frizz index and aspect ratio after 90 minutes compared with those treated with hair treatment of comparative example 17. This suggest that the liquid aryl group-containing polyorganosiloxane of the present invention helped to significantly control hair frizziness apparition and aspect ratio of tresses exposed at high relative humidity for a long time.

INDUSTRIAL APPLICABILITY

The liquid aryl group-containing polyorganosiloxane according to the present invention may be designed as an oil agent having a relatively low molecular weight, displays a high refractive index of 1.55 or greater, has superior compatibility with an oil agent or an oleophilic component, and, furthermore, when mixed with other oil agents, turbidity that accompanies hydrolysis does not occur even when stored for an extended period of time. Therefore, the liquid aryl group-containing polyorganosiloxane according to the present invention can be used in known silicone oil applications, particularly in applications other than those of cosmetic products requiring high refractive indices. Furthermore, in addition to providing soft focus and similar optical characteristics, changes in color can be suppressed by compounding the liquid aryl group-containing polyorganosiloxane according to the present invention with a pigment or a colorant. Thus, the liquid aryl group-containing polyorganosiloxane according to the present invention can also be compounded in coatings and similar compositions for use in non-cosmetic compositions. Moreover, while not limited thereto, specific industrial applications include various lubricating oils, heat mediums, hydraulic fluids, slip agents, slide agents, bleed oils, antifouling coatings, stress mitigating agents acting by being added to an organic resin, light wave guides•optic fiber, liquid developers, high refractive index diluents, and liquid lenses. Furthermore, in cases where mixed with another curable silicone oil, the liquid aryl group-containing polyorganosiloxane according to the present invention substantially increases the overall refractive index of the composition and has superior compatibility and, as a result, is useful as an optical coating, a sealing material for a semiconductor element, LED, or the like of LCD backlights, traffic signals, large outdoor displays, advertising billboards, and the like, a raw material or additive in a reflector, an optic case, an optical-use silicone lens, or the like. Note that these are typical applications of optics-use high refractive index silicones.

The invention claimed is:

1. A liquid aryl group-containing polyorganosiloxane comprising an arylsiloxy unit represented by $RSiO_{3/2}$, wherein R is an aryl group, and wherein the arylsiloxy unit constitutes from 20 to 50 mol % of all the siloxy units constituting the polyorganosiloxane, and an average number of moles of aryl groups per one mole of Si atoms in the polyorganosiloxane is within a range of 1.20 to 1.65, wherein the liquid aryl group-containing polyorganosiloxane is represented by the following average composition formula (1-1):

Average composition formula (1-1):

$$(R^4_2R^6SiO_{1/2})_{a'}(R^4R^7SiO_{2/2})_{b'}(R^4SiO_{3/2})_{c'} \quad (1\text{-}1)$$

wherein, $R^4$ is a phenyl group or a naphthyl group, $R^6$ and $R^7$ are each independently a monovalent organic group or a hydrogen atom, $0.10 \leq b' \leq 0.40$ and $0.20 \leq c' \leq 0.50$, $a'+b'+c'=1.0$, and a number of moles of phenyl groups or naphthyl groups per one mole of Si atoms in the polyorganosiloxane of a' to c' is, on average, in a range of 1.20 to 1.65.

2. The liquid aryl group-containing polyorganosiloxane according to claim 1, in which a refractive index is not less than 1.50, and a weight average molecular weight as measured by gel permeation chromatography (GPC) is in a range of 500 to 2,000.

3. An aryl group-containing polyorganosiloxane composition comprising: (A) a liquid aryl group-containing polyorganosiloxane according to claim 1, and (B) an oil agent different from component (A), wherein an overall refractive index of the composition is not less than 1.45, and an overall viscosity at 25° C. of the composition is in a range of 100 to 100,000 mPa·s.

4. The aryl group-containing polyorganosiloxane composition according to claim 3, wherein the component (B) is a phenyl group-containing organopolysiloxane represented by structural formula (2-1) or structural formula (2-2) below:

Structural formulae:

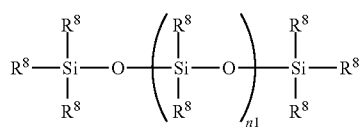
(2-1)

-continued

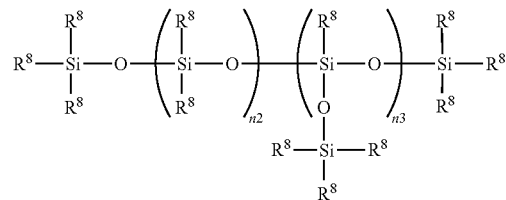
(2-2)

wherein each $R^8$ is independently a group selected from a phenyl group, an aralkyl group, a hydrogen atom, a hydroxyl group, or a fluorinated alkyl group or an alkyl group having from 1 to 20 carbons and, in terms of molar ratio, at least 50% of the $R^8$ moieties are phenyl groups; n1 or n2 is a number in a range of 0 to 1,000; and n3 is a number in a range of 1 to 1,000.

5. A cosmetic composition comprising a liquid aryl group-containing polyorganosiloxane composition according to claim 3.

6. The cosmetic composition according to claim 5, further comprising: (C) one or more types of oleophilic cosmetic raw material.

7. The aryl group-containing polyorganosiloxane composition according to claim 3, wherein the liquid aryl group-containing polyorganosiloxane has a refractive index not less than 1.50, and a weight average molecular weight as measured by gel permeation chromatography (GPC) is in a range of 500 to 2,000.

8. A cosmetic composition comprising a liquid aryl group-containing polyorganosiloxane according to claim 1.

9. The cosmetic composition according to claim 8 that is a makeup cosmetic composition, a hair cosmetic composition, or a skin cosmetic composition.

10. A method for producing a liquid aryl group-containing polyorganosiloxane comprising: a step (I) of mixing (A-1) at least one organosilicon compound selected from an aryl group-containing polyorganosiloxane that is solid at 25° C. and that comprises an arylsiloxy unit represented by $RSiO_{3/2}$, wherein R is an aryl group, wherein the arylsiloxy unit constitutes not less than 50 mol % of all the siloxy units constituting the polyorganosiloxane; an organosilane represented by $RSiX_{3-n4}(OR^9)_{n4}$, wherein R is an aryl group, X is a halogen atom, $R^9$ are each independently a hydrogen atom or an alkyl group having from 1 to 6 carbons, and n4 is a number within a range of 0 to 3; and a condensation reaction product of said organosilane;

(A-2) an aryl group-containing organopolysiloxane oligomer represented by structural formula (3) below:

Structural formula (3):

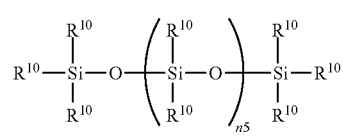
(3)

wherein $R^{10}$ are each independently a monovalent organic group and, at least 50% of the $R^{10}$ moieties are aryl groups, and n5 is a number in a range of 0 to 10; and (A-3) a catalyst; and a step (II) of reacting the mixture obtained in step (I) to obtain an equilibration reaction;

wherein the liquid aryl group-containing polyorganosiloxane includes an arylsiloxy unit represented by $RSiO_{3/2}$, wherein R is an aryl group, and wherein the arylsiloxy unit constitutes from 20 to 50 mol % of all the siloxy units constituting the polyorganosiloxane, and an average number of moles of aryl groups per one mole of Si atoms in the polyorganosiloxane is within a range of 1.20 to 1.65.

11. The method for producing the liquid aryl group-containing polyorganosiloxane according to claim 10, in which the liquid aryl group-containing polvorganosiloxane has a refractive index is not less than 1.50, and a weight average molecular weight as measured by gel permeation chromatography (GPC) is in a range of 500 to 2,000.

12. A cosmetic composition comprising a liquid aryl group-containing polyorganosiloxane comprising an arylsiloxy unit represented by $RSiO_{3/2}$, wherein R is an aryl group, and wherein the arylsiloxy unit constitutes from 20 to 50 mol % of all the siloxy units constituting the polyorganosiloxane, and an average number of moles of aryl groups per one mole of Si atoms in the polyorganosiloxane is within a range of 1.20 to 1.65, wherein the liquid aryl group-containing polyorganosiloxane is present in the cosmetic composition in an amount of from 0.5-50 wt. % based on the total weight of the cosmetic composition.

13. The cosmetic composition according to claim 12, further comprising: (C) one or more types of oleophilic cosmetic raw material.

14. The cosmetic composition according to claim 12 that is a makeup cosmetic composition, a hair cosmetic composition, or a skin cosmetic composition.

* * * * *